(12) United States Patent
Dessen et al.

(10) Patent No.: US 10,751,363 B2
(45) Date of Patent: Aug. 25, 2020

(54) USE OF ALIGINATE OLIGOMERS AND CFTR MODULATORS IN TREATMENT OF CONDITIONS ASSOCIATED WITH CFTR DYSFUNCTION

(71) Applicant: AlgiPharma AS, Sandvika (NO)

(72) Inventors: Arne Dessen, Røyken (NO); Astrid Hilde Myrset, Oslo (NO); Philip Rye, Eiksmarka (NO)

(73) Assignee: AlgiPharma AS, Sandvika (NO)

( * ) Notice: Subject to any disclaimer, the term of this patent is extended or adjusted under 35 U.S.C. 154(b) by 0 days.

(21) Appl. No.: 15/560,984

(22) PCT Filed: Mar. 23, 2016

(86) PCT No.: PCT/EP2016/056458
§ 371 (c)(1),
(2) Date: Sep. 22, 2017

(87) PCT Pub. No.: WO2016/151051
PCT Pub. Date: Sep. 29, 2016

(65) Prior Publication Data
US 2018/0055873 A1    Mar. 1, 2018

(30) Foreign Application Priority Data
Mar. 23, 2015 (GB) .................................. 1504878.8

(51) Int. Cl.
| A61K 31/734 | (2006.01) |
| A61K 31/443 | (2006.01) |
| A61K 31/4245 | (2006.01) |
| A61K 31/47 | (2006.01) |
| A61K 45/06 | (2006.01) |
| A61K 31/4164 | (2006.01) |
| A61K 31/405 | (2006.01) |
| A61K 31/496 | (2006.01) |
| A61K 31/4965 | (2006.01) |
| A61K 31/43 | (2006.01) |
| A61K 31/7036 | (2006.01) |

(52) U.S. Cl.
CPC .......... *A61K 31/734* (2013.01); *A61K 31/405* (2013.01); *A61K 31/4164* (2013.01); *A61K 31/4245* (2013.01); *A61K 31/43* (2013.01); *A61K 31/443* (2013.01); *A61K 31/47* (2013.01); *A61K 31/496* (2013.01); *A61K 31/4965* (2013.01); *A61K 31/7036* (2013.01); *A61K 45/06* (2013.01)

(58) Field of Classification Search
CPC ........................... A61K 31/734; A61K 31/443
See application file for complete search history.

(56) References Cited

U.S. PATENT DOCUMENTS

| 5,169,840 | A | 12/1992 | Otterlei et al. | |
| 6,121,441 | A | 9/2000 | Simensen et al. | |
| 7,495,103 | B2 | 2/2009 | Hadida-Ruah et al. | |
| 8,741,925 | B2 | 6/2014 | Hadida-Ruah et al. | |
| 2009/0010914 | A1* | 1/2009 | Taylor | A61K 9/007 424/94.61 |
| 2010/0305062 | A1* | 12/2010 | Onsoyen | A01N 43/16 514/54 |
| 2011/0288122 | A1 | 11/2011 | Van Goor et al. | |

FOREIGN PATENT DOCUMENTS

| EP | 1 681 051 A1 | 7/2006 |
| KR | 20150000110 A | 1/2015 |
| WO | WO 89/08448 A1 | 9/1989 |
| WO | WO 91/11205 A1 | 8/1991 |
| WO | WO 94/09124 A1 | 4/1994 |
| WO | WO 03/045402 A1 | 6/2003 |
| WO | WO 2004/011628 A1 | 2/2004 |
| WO | WO 2006/002421 A2 | 1/2006 |
| WO | WO 2007/039754 A1 | 4/2007 |
| WO | WO 2007/039760 A2 | 4/2007 |
| WO | WO 2007/056341 A1 | 5/2007 |
| WO | WO 2007/134279 A2 | 11/2007 |
| WO | WO 2008/125828 A2 | 10/2008 |
| WO | WO 2009/038683 A2 | 3/2009 |
| WO | WO 2009/064959 A1 | 5/2009 |
| WO | WO 2009/068841 A2 | 6/2009 |
| WO | WO 2009/073757 A1 | 6/2009 |

(Continued)

OTHER PUBLICATIONS

Mayo Clinic entry for cystic fibrosis, website https://www.mayoclinic.org, accessed online on Feb. 15, 2019. (Year: 2019).*
Ren et al. Molecular Biology of the Cell, 2013, 24(19), p. 3016-3024. (Year: 2013).*
PubChem entry for Lumacaftor, https://pubchem.ncbi.nlm.nih.gov, accessed online on Feb. 15, 2019. (Year: 2019).*
Al-Khedairy 2006 "In vitro release study on capsules and tablets containing enteric—coated granules prepared by wet granulation" *Iraqi J. Pharm. Sci.* 15(1): in 4 pages.
Clancy et al. 2013 "Multicenter Intestinal Current Measurements in Rectal Biopsies from CF and Non-CF Subjects to Monitor CFTR Function" *PLOS* 8(9): e73905 (in 13 pages).

(Continued)

*Primary Examiner* — Jonathan S Lau
(74) *Attorney, Agent, or Firm* — Knobbe, Martens, Olson & Bear, LLP

(57) ABSTRACT

A method is for the treatment of a condition in a subject, which arises from or is associated with CFTR dysfunction. The method includes administering to the subject an effective amount of a CFTR modulator together with an effective amount of an alginate oligomer. The condition can be cystic fibrosis (CF), non-compound CFTR gene mutation heterozygosity, abnormal mucus clearance in the respiratory tract and/or breathing difficulties resulting from chronic particulate inhalation, COPD, chronic bronchitis, emphysema, bronchiectasis, asthma or chronic sinusitis, or a complication of any of these.

14 Claims, 3 Drawing Sheets

(56) References Cited

FOREIGN PATENT DOCUMENTS

| WO | WO 2009/076141 A2 | 6/2009 |
| --- | --- | --- |
| WO | WO 2009/076142 A2 | 6/2009 |
| WO | WO 2010/019239 A2 | 2/2010 |
| WO | WO 2010/037066 A2 | 4/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/138484 A2 | 12/2010 |
| WO | WO 2010/139957 A1 | 12/2010 |
| WO | WO 2011/019413 A1 | 2/2011 |
| WO | WO 2011/050325 A1 | 4/2011 |
| WO | WO 2011/072241 A1 | 6/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2011/133953 A1 | 10/2011 |
| WO | WO 2011/133956 A1 | 10/2011 |
| WO | WO 2011/146901 A1 | 11/2011 |
| WO | WO 2012/027731 A2 | 3/2012 |
| WO | WO 2015/128495 A1 | 9/2015 |

OTHER PUBLICATIONS

De Boeck et al. 2011 "New clinical diagnostic procedures for cystic fibrosis in Europe" *Journal of Cystic Fibrosis* 10(2): S53-S66.

Derichs et al. 2010 "Intestinal current measurement for diagnostic classification of patients with questionable cystic fibrosis: validation and reference data" *Thorax* 65: 594-599.

Derichs 2013 "Targeting a genetic defect: cystic fibrosis transmembrane conductance regulator modulators in cystic fibrosis" *Eur. Respir. Rev.* 127: 58-65.

ErtesvÅg et al. 1999 "Mannuronan C-5-Epimerases and their application for in Vitro and in Vivo design of new alginates useful in biotechnology" *Metabolic Engineering* 1: 262-269.

Gimmestad et al. 2006 "Identification and Characterization of an *Azotobacter vinelandii* Type I Secretion System Responsible for Export of the AlgE-Type Mannuronan C-5—Epimerases" *Journal of Bacteriology* 188(15): 5551-5560.

Gimmestad et al. 2003 "The *Pseudomonas fluorescens* AlgG protein, but not its mannuronan C-5-Epimerase activity, is needed for alginate polymer formation" *Journal of Bacteriology* 185(12): 3515-3523.

Illek et al. 1999 "Defective function of the cystic fibrosis-causing missense mutation G551D is recovered by genistein" *Am. J. Physiol* 46: C833-C839.

Khan et al. 2013 "A Novel Multilayered Multidisk Oral Tablet for Chronotherapeutic Drug Delivery" *BioMed Research International* 2013: 1-17.

Norez et al. 2008 "Proteasome-Dependent Pharmacological Rescue of Cystic Fibrosis Transmembrane Conductance Regulator Revealed by Mutation of Glycine 622" *The Journal of Pharmacology and Experimental Therapeutics* 325(1): 89-99.

Pedemonte et al. 2005 "Small-molecule correctors of defective ΔF508-CFTR cellular processing identified by high-throughput screening" *The Journal of Clinical Investigation* 115(9): 2564-2571.

Pedemonte et al. 2005 "Phenylglycine and sulfonamide correctors of defective ΔF508 and G551D cystic fibrosis transmembrane conductance regulator Chloride-Channel Gating" *Molecular Pharmacology* 67(5): 1797-1807.

Pettit and Fellner 2014 "CFTR modulators for the treatment of cystic fibrosis" *Pharmacy & Therapeutics* 39(7): 500-511.

Pritchard et al. 2004 "The effect of a novel alginate oligomer on the structure of mucin and sputum" *Abstracts of the Interscience Conference on Antimicrobial Agents and Chemotherapy* 54: B-1360.

Remminghorst & Rehm 2006 "Bacterial alginates: from biosynthesis to applications" *Biotechnol Lett* 28: 1701-1712.

Strugala et al. 2004 "Bioactive properties of epimerized alginates" *Gums and Stabilisers for the Food Industry* 12: 84-94.

Van Goor et al. 2006 "Rescue of ΔF508-CFTR trafficking and gating in human cystic fibrosis airway primary cultures by small molecules" *Am J Physiol Lung Cell Mol Physiol* 290: L1117-L1130.

Van Goor et al. 2009 "Rescue of CF airway epithelial cell function in vitro by a CFTR potentiator, VX-770" *PNAS* 106(44): 18825-18830.

Rye, et al. 2014 "Alginate oligosaccharides for the treatment of cystic fibrosis" *International Symposium on Polymer Therapeutics:*, Valencia Spain, (in 25 pages).

Khan, S. et al. 2012 "Overcoming Drug Resistance with Alginate Oligosaccharides Able to Potentiate the Action of Selected Antibiotics" *Antimicrobial Agents and Chemotherapy* 56(10): 5134-5141.

Cystic Fibrosis Foundation 2017 "CFTR Mutation Classes and Getting to Know your Mutations: a CFTR Mutation Fact Sheet" (in 2 pages), available on the World-Wide-Web at: cff.org/What-is-CF/Genetics/Know-Your-CFTR-Mutations-Infographic.pdf.

Leal et al. 2017 "Physicochemical properties of mucus and their impact on transmucosal drug delivery" *Int J Pharm* 532: 555-572.

\* cited by examiner

| Structure | Activity | Name |
|---|---|---|
| | potentiator | VRT-532 |
| | potentiator | PG-01 |
| | potentiator | SF-03 |
| | potentiator | UCCF-853 |
| | potentiator | ΔF508act-02 |
| | potentiator | Genistein |
| | potentiator | NS004 |

| Structure | Activity | Name |
|---|---|---|
| | potentiator | UCCF-029 |
| | potentiator | UCCF-180 |
| | potentiator | UCCF-152 |
| | corrector | corr-3a |
| | corrector | VRT-640 |
| | corrector | VRT-325 |
| | corrector | corr-4a |
| | potentiator | felodipine |
| | potentiator | DHP-229 |
| | potentiator | DHP-256 |

VRT-422 potentiator

USE OF ALGINATE OLIGOMERS AND CFTR MODULATORS IN TREATMENT OF CONDITIONS ASSOCIATED WITH CFTR DYSFUNCTION

FIELD OF THE INVENTION

The present invention relates to alginate oligomers for use together with (or in combination or conjunction with) a cystic fibrosis transmembrane conductance regulator (CFTR) modulator in treating a condition in a human patient arising from or associated with CFTR ion channel dysfunction (CFTR dysfunction). The combination therapy of the invention may be more effective (e.g. more efficacious) than the use of these agents alone, e.g. through the potentiation of the remedial effects of CFTR modulators on CFTR dysfunction (e.g. by enhancing clinical efficacy or improving the effectiveness of the CFTR modulator against its biological target) or by permitting more effective, safer or convenient routes of administration to be used. The combined use may further permit the treatment of patient groups considered to be poorly responsive to CFTR modulators, e.g. patients in which a pathological phenotype associated with CFTR dysfunction has become well established.

BACKGROUND

The CFTR is a transmembrane protein found in the epithelial cells of mucosal surfaces. It is involved in the transport of chloride and bicarbonate ions across epithelial membranes where it functions as an ATP-gated ion channel and thereby also influences the balance of other ions such as sodium across such membranes. When an appropriate ionic balance is maintained, the mucus layer of the mucosal surface displays a normal structure and composition and therefore behaves and functions normally. Insufficient numbers of functional CFTR ion channels at the epithelial cell surface, e.g. as a consequence of mechanisms which cause reduced numbers of CFTR at the cell surface, and/or insufficient ion channel activity in the population of CFTR that are present at the cell surface, results in the pathological state referred to as CFTR (ion channel) dysfunction. The perturbations in ionic balance at mucosal surfaces caused by CFTR dysfunction manifest in stagnant mucus in all organs where mucus is formed, and thickened secretions from glands in the liver and the pancreas. The presence of this stagnant mucus in the lungs, paranasal sinuses, gastrointestinal (GI) tract, pancreas, liver and female and male reproductive systems leads to a plethora of clinical conditions associated not only with poor quality of life but also morbidity and mortality. Indeed, in cystic fibrosis, the most recognisable disease associated with CFTR dysfunction, sufferers typically succumb to a complication directly associated with this stagnant mucus.

CFTR dysfunction, or more specifically CFTR ion channel dysfunction (which terms are considered synonymous for the purposes of the invention and are therefore used interchangeably herein) typically arises from a defect in the CFTR which affects its activity and/or its cellular processing and delivery (trafficking) to the cell surface. Such defects may in many cases be due to mutations in the CFTR (i.e due to an underlying genetic defect), but can also arise due to extrinsic factors which may for example cause aberrant or impaired expression of the CFTR at the cell surface. Taking these various "defects" together, it can be seen that, broadly speaking, six classes of "mechanism" underlying defective CFTR function can be recognised, and CFTR dysfunction may arise from one or more of these. Class I mechanisms involve the presence of a premature stop codon in the CFTR mRNA transcript and give rise to truncated CFTR with reduced function and/or which are poorly transported to the cell membrane. Class II mechanisms involve impaired intracellular processing of full length CFTR translation products which interferes with the CFTR's route to the cell membrane (e.g. misfolding, defective post-translational modification, inappropriate intracellular protein sorting, degradation prior to reaching the cell membrane). Class III mechanisms involve disordered ion channel regulation (e.g. poor activation by ATP or cAMP, reduced channel open time). Class IV mechanisms involve reduced channel conductance. Class V mechanisms involve splicing defects in the transcription of CFTR mRNA or reduced CFTR mRNA transcription per se. Like Class I, Class V mechanisms can give rise to CFTR with reduced function and/or reduced quantities of CFTR in the cell membrane. Class VI mechanisms involve accelerated turnover of CFTR protein at the cell membrane which reduces the quantities of CFTR in the cell membrane.

CF is an autosomal recessive genetic disease of humans arising from mutations in the CFTR which result in CFTR dysfunction. CF-causing mutations may be classified within different "mechanistic" classes as set out above and thus the aetiology of CF is extremely diverse.

In the lungs of CF patients, the dense, attached and intractable mucus caused by the CFTR dysfunction is insufficiently cleared by the mucociliary clearance system, and accumulates in the airways. This makes patients susceptible to chronic lung infections and inflammation (pneumonia), which causes bacteria, bacterial biofilm, and cell debris to become intermixed with the mucus and leads to increased mucus viscosity. In turn this eventually leads to permanent lung damage and remodelling and further to pulmonary hypertension, heart failure, and respiratory failure. Infection by *Staphylococcus aureus, Haemophilus influenzae, Pseudomonas aeruginosa, Mycobacterium avium* complex and *Aspergillus fumigatus* are common. Abnormal mucus higher up in the respiratory tract (e.g. in the bronchi) can also be susceptible to infection which in turn may lead to inflammation of mucosal surfaces (e.g. bronchitis). Response to antibiotics is often poor.

In the paranasal sinuses the abnormal mucus results in frequent blockages leading to facial pain, headaches and abnormal nasal drainage. The sinuses are often exacerbated by infection, to which the abnormal mucus is highly susceptible and this may lead to acute, subacute and chronic sinusitis (also known as rhinosinusitis). Overgrowth of the nasal tissue (nasal polyps) may also result as a consequence of the chronic inflammatory state induced from chronic sinus infection. These polyps can block the nasal passages and increase breathing difficulties.

In the GI tract the attached and abnormal mucus is thought to result in intestinal pain and even full obstruction. In neonatal subjects mucus can combine with meconium to plug the ileum (meconium ileus). In older patients intestinal blockage by intussusception and distal intestinal obstruction syndrome (DIOS) of the distal ileum is often seen. Bacterial overgrowth and complications associated with the stagnant mucus may also occur.

In the pancreas, thickened and attached mucus in exocrine secretions often blocks the pancreatic duct and reduces the amount of digestive enzymes and bile entering the GI tract. This causes accumulation of digestive enzymes in the pancreas which in turn reduces the ability of a patient to retrieve dietary nutrients (nutrient malabsorption) and can cause inflammation, and irreversible damage to the pancreas. Such inflammation and damage results in pancreatitis (both acute and chronic) and ultimately atrophy of the exocrine glands and fibrosis. Damage of the pancreas can also lead to loss of the islet cells, leading to cystic fibrosis-related diabetes.

In the liver thickened bile secretions and mucus lining may block the bile ducts, causing gallstones, and lead to liver damage and ultimately cirrhosis.

Fertility of healthy females is regulated in part by the properties of the mucus in the reproductive system, especially the mucus of the cervix. The vas deferens of male mammals contains mucus that can obstruct the vas deferens if that mucus is abnormal. The abnormal mucus caused by mutation in the CFTR gene has therefore been connected with both female and male infertility.

There is currently no cure for the underlying genetic causes of CF, although the life-threatening lung and liver disease can sometimes be resolved with a successful lung or liver transplant. Lung transplants in CF patients are however not always successful because lung infection can recur shortly after transplantation. This is usually a consequence of the use of immunosuppressant drugs to promote establishment of the transplant making the transplant susceptible to the infections that remain in the patient's respiratory tract above the newly transplanted lungs.

Other conditions beyond CF may also be characterised by, or associated with, CFTR dysfunction. In recent years it has been recognised that even in subjects who do not suffer from classical or "overt" CF (that is who do not carry homozygous or compound heterozygous mutations in their CFTR alleles) CFTR dysfunction at epithelial cell layers can occur and give rise to the abnormal mucus and endocrine secretions that are like or similar to those that characterise CF. Thus, for example such subjects may carry one or more CFTR mutations, but the mutations do not result in CFTR dysfunction of sufficient severity to qualify as CF as such. This results in abnormal mucus clearance which in turn may lead to or at least contribute to, inter alia, breathing difficulties, CF-like symptoms and complications, and chronic inflammatory respiratory disorders including COPD (and its subtypes chronic bronchitis and emphysema), bronchiectasis, asthma and chronic sinusitis. Accordingly, diseases and disorders (or more generally a "condition") associated with CFTR dysfunction may include not only CF, but also other conditions involving respiratory dysfunction (more generally other respiratory disorders), and in particularly disorders involving pulmonary obstruction, including particularly asthma.

In some instances CFTR dysfunction is seen in subjects that have non-compound heterozygous mutant CFTR alleles. In such subjects the inherited dysfunction is mild and so is insufficient to manifest as overt CF, but is sufficient to result in mucus that is more dense, attached and intractable than normal, as well as secretions from glands in the liver and the pancreas that are thicker than normal. As discussed above in the context of overt CF, in the respiratory tract, such mucus is often insufficiently cleared by the mucociliary clearance system and so accumulates in the airways and may lead to further symptoms and complications. Similarly, the thickened mucus and exocrine secretions in the paranasal sinuses, gastrointestinal (GI) tract, pancreas, liver and female and male reproductive systems of these subjects may be sufficient to lead to mild forms of the plethora of clinical conditions associated with overt CF.

In other instances it has been shown that CFTR dysfunction may be acquired. It is now known that the chronic inhalation of particulate irritants, e.g. smoke particles (tobacco, wood etc.), pollution, dust (asbestos, cotton, coal, stone, animal droppings etc.) and spores, can result in reduced CFTR ion channel activity (e.g. reduction in gating and/or conductance) at epithelial cell surfaces carrying the receptor. It will be seen that in subjects who display mild CFTR dysfunction because of an inherited defect, these deleterious effects of environmental factors on CFTR may be more pronounced clinically. This acquired dysfunction and the effects on mucus are thought to contribute to the progression of chronic inflammatory disorders, e.g. COPD, CB, emphysema, bronchiectasis and chronic sinusitis in these subjects. It has also been recognised that the intracellular processing of CFTR can be interfered with and the turnover of CFTR at the cell membrane can be accelerated during chronic airway inflammation, e.g. as seen in COPD (and its subtypes chronic bronchitis and emphysema), bronchiectasis and chronic sinusitis.

In all of these contexts CFTR dysfunction in the respiratory tract may result in the dense, attached and intractable mucus characteristic of CF which is insufficiently cleared by the mucociliary clearance system and which accumulates in the airways. This makes patients with acquired CFTR dysfunction susceptible to the respiratory symptoms and complications experienced by CF patients, including those shared with COPD, CB, emphysema, asthma and chronic sinusitis.

Until recently, pharmaceutical intervention in CF and other conditions associated with CFTR dysfunction has been restricted to management of secondary symptoms and conditions and very few options are available to address the main underlying cause of those conditions: the abnormal mucus and in turn CFTR dysfunction. In addition to pharmaceutical interventions, patients with CFTR dysfunction, in particular CF patients, will typically undergo physiotherapy to the chest and/or abdomen designed to alleviate the lung and/or GI complications, particularly in relation to assisting the clearing of the lungs and/or breathing. Such physiotherapy techniques may include one or more of active cycle of breathing techniques (ACBT), postural drainage, manual percussion and vibration, autogenic drainage (AD), high frequency chest wall oscillation (HFCWO), positive expiratory pressure (PEP), and oscillating positive expiratory pressure devices (Oscillating PEP).

In patients with CFTR dysfunction, lung complications are typically managed through antibiotic, antifungal, anti-inflammatory and bronchodilator treatment regimes, the nutrient malabsorption caused by pancreatic complications can be treated with digestive enzyme supplements and cystic fibrosis-related diabetes may be treated by a combination of oral antidiabetic drugs (e.g. the sulfonylureas, biguanides and thiazolidinediones) and i.v. insulin. Liver complications are typically tackled as for other patients with liver disease, but little can be done once damage has occurred to any of these organs.

A few approaches have been developed to address the abnormalities of the mucus, principally its elevated viscosity. These include dornase alfa (a DNase enzyme), hypertonic saline, mannitol, acetylcysteine, dextran and denufosol (an agonist of the P2Y2 subtype of purinergic receptors, an alternative chloride channel in the lung). However, these treatments only show limited efficacy and are limited to the lung. Alginate oligomers have also been shown to be capable of reducing the viscosity of sputum from COPD patients and cervical mucus (WO 2007/039754, WO 2007/039760; WO2008/125828) and the use of alginate oligomers to treat CF, female infertility and hyperviscous mucus in the gut has been proposed on this basis.

Alginates are naturally occurring polysaccharides that have been found to have a number of uses, both clinical (e.g. in wound dressings, as drug carriers and in anti-heartburn preparations) and non-clinical (e.g. in food preparation). They are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate).

Alginates have been isolated from marine brown algae (e.g. certain species of *Durvillea, Lessonia* and *Laminaria*) and bacteria such as *Pseudomonas aeruginosa* and *Azotobacter vinelandii*. Other pseudomonads (e.g. *Pseudomonas fluorescens, Pseudomonas putida*, and *Pseudomonas mendocina*) retain the genetic capacity to produce alginates but in the wild they do not produce detectable levels of alginate. By mutation these non-producing pseudomonads can be induced to produce stably large quantities of alginate.

Alginate is synthesised as polymannuronate and G residues are formed by the action of epimerases (specifically C-5 epimerases) on the M residues in the polymer. In the case of alginates extracted from algae, the G residues are predominantly organised as G blocks because the enzymes involved in alginate biosynthesis in algae preferentially introduce the G neighbouring another G, thus converting stretches of M residues into G-blocks. Elucidation of these biosynthetic systems has allowed the production of alginates with specific primary structures (WO 94/09124, Gimmestad, M et al, Journal of Bacteriology, 2003, Vol 185(12) 3515-3523 and WO 2004/011628).

Alginates are typically isolated from natural sources as large high molecular weight polymers (e.g. an average molecular weight in the range 300,000 to 500,000 Daltons). It is known, however, that such large alginate polymers may be degraded, or broken down, e.g. by chemical or enzymatic hydrolysis to produce alginate structures of lower molecular weight. Alginates that are used industrially typically have an average molecular weight in the range of 100,000 to 300,000 Daltons (such alginates are still considered to be large polymers) although alginates of an average molecular weight of approximately 35,000 Daltons have been used as excipients in pharmaceuticals.

In addition to a proposed use of alginate oligomers of smaller size (molecular mass) to reduce the viscosity of hyperviscous sputum such as occurs in sufferers of cystic fibrosis and other respiratory diseases (see WO 2007/039754 and WO 2008/125828), such oligomers have also been proposed for other clinical uses, to combat biofilm (WO 2009/068841) and multidrug resistant bacteria (WO 2010/13957).

More recently the new pharmaceutical class of "CFTR modulators" has emerged offering a pharmaceutical intervention at the level of CFTR dysfunction, in particular in the treatment of CF (Derichs, N., Eur. Respir. Rev., 2013, 22(127), 58-65; Petit, R. S. and Fellner, C., Pharmacy and Therapeutics, 2014, 39(7), 500-511). Also known as "CFTR modifiers", which terms are used interchangeably herein, CFTR modulators are small molecules which can redress, at least partially, a mechanism of CFTR dysfunction from one or more classes of CFTR dysfunction. Present CFTR modulators fall into three main groups: CFTR potentiators, CFTR correctors and read-through agents.

CFTR potentiators are CFTR modulators which increase the activity of the CFTR ion channel present on the epithelial cell surface (e.g. by increasing the open probability or conductance of the channel) and thus have utility in contexts in which a Class III or a Class IV dysfunction is present (i.e. a dysfunction caused by gating or conductance problems in the CFTR at the cell surface). Prototypical examples of CFTR potentiators are ivacaftor (VX-770; N-(2,4-di-tert-butyl-5-hydroxyphenyl)-1,4-dihydro-4-oxoquinoline-3-carboxamide) and VRT-532 (4-methyl-2-(5-phenyl-1H-pyrazol-3-yl)-phenol) of Vertex Pharmaceuticals).

CFTR correctors are CFTR modulators which increase the amount of CFTR protein delivered or retained at the epithelial cell surface. These molecules may achieve this effect in a variety of ways in view of the variety of defects in the processing of CFTR that can cause reduced quantities of CFTR at the epithelial cell surface. For instance, certain CFTR correctors can act as a chaperone facilitating proper folding and post-translational modification of CFTR, protecting CFTR from premature degradation, facilitating intracellular targeting of CFTR and reversing accelerated turnover of CFTR at the cell membrane. Correctors thus have utility in the context of Class II, Class V and Class VI dysfunctions. Prototypical examples of CFTR correctors include lumacaftor (VX-809) and tezacaftor (VX-661) of Vertex Pharmaceuticals and N6022 (3-[1-(4-carbamoyl-2-methylphenyl)-5-(4-imidazol-1-ylphenyl)pyrrol-2-yl]propanoic acid).

Read-through agents (also known as "premature stop codon suppressors" (PSC suppressors) or "premature termination codon suppressors" (PTC suppressors, which terms are used interchangeably herein) are CFTR modulators which cause the translation machinery of the cell to pass over any premature termination codon in the CFTR mRNA thereby increasing the amount of substantially full length and functional CFTR produced. Read-through agents thus have utility in the context of Class I dysfunctions. Prototypical examples of read-through agents include ataluren (PTC124) of PTC Therapeutics and gentamicin.

Further CFTR modulators are disclosed in WO2006/002421, WO2007/056341 WO2007134279, WO2009038683, WO2009064959, WO2009073757, WO2009076141, WO2009076142, WO2010019239, WO2010037066, WO2010048526, WO2010053471, WO2010054138, WO2010138484, WO2011019413, WO2011050325, WO2011072241, WO2011127241, WO2011127290, WO2011133751, WO2011133951, WO2011133953, WO2011133956, WO2011146901, Pedemonte, N., et al., J Clin Invest. 2005; 115(9):2564-2571, Van Goor, F. et al., Am J Physiol Lung Cell Mol Physiol 2006, 290: L1117-L1130, and Pedemonte, N., et al., Molecular Pharmacology, 2005 vol. 67 no. 5 1797-1807 the content of which is incorporated herein by reference, and FIG. 3.

Experience with CFTR modulators to date has been based on systemic administration via oral or injection routes, at least in part in order to avoid potential bioavailability complications arising from the possible "barrier effect" of the abnormal mucus which results from CFTR dysfunction, namely that the presence of the abnormal mucus may impede access of the modulator to the epithelial cells (especially in the respiratory system where bioburden is significantly greater than at other mucosal surfaces, but also in the GI tract where the mucus layer is comparatively thicker than at other mucosal surfaces). Moreover, it has been suggested that younger patients will respond better to this class of therapeutic agent because the younger a patient is, the less damage has accrued. More particularly, in younger patients there has been less time for a CFTR dysfunction phenotype (especially one including chronic infection, chronic inflammation and airway remodelling) to become established and to develop into a phenotype that can interfere with the action of CFTR modulators. Administration by inhalation, for instance, to a patient with a well-established CFTR dysfunction phenotype would, for example, be considered very challenging.

Although existing developments in this field show promise, there is a continuing need for improved pharmaceutical interventions, including treatment regimens, for conditions arising from or associated with CFTR dysfunction and, specifically, the abnormal mucus of patients with CFTR dysfunction (e.g. patients with CF, patients with abnormal mucus clearance in the respiratory tract and/or breathing difficulties resulting from chronic particulate inhalation, patients with chronic inflammatory respiratory disorders, e.g. COPD (and its subtypes chronic bronchitis and emphysema), bronchiectasis, asthma and chronic sinusitis, and/or patients with non-compound CFTR gene mutation) especially those conditions associated with the lung, the GI tract, the pancreas, the liver and the reproductive system.

SUMMARY OF THE INVENTION

It is now proposed to use alginate oligomers together with (or in combination or conjunction with) a CFTR modulator in treating a condition in a human patient arising from or associated with CFTR dysfunction. Such combination therapies may represent more effective (e.g. more efficacious) treatments than the use of these agents alone, e.g. through the potentiation of the remedial effects of CFTR modulators on CFTR dysfunction (e.g. by enhancing clinical efficacy, or improving effectiveness of the CFTR modulator against its biological target) or by permitting more effective, safer or convenient routes of administration to be used (e.g. inhalation) or by increasing bioavailability of the CFTR modulator, e.g. enteral bioavailability. The combined use may further permit the treatment of patient groups considered to be poorly responsive to CFTR modulators, e.g. patients in which a pathological phenotype associated with CFTR dysfunction has become well established.

Accordingly, in a first aspect the invention provides an alginate oligomer for use together with (or in combination or conjunction with) a CFTR modulator in the treatment of a condition in a subject arising from or associated with CFTR dysfunction.

The invention further provides a method for the treatment of a condition in a subject arising from or associated with CFTR dysfunction, said method comprising administering to said subject an effective amount of a CFTR modulator together with (or in combination or conjunction with) an effective amount of an alginate oligomer.

The subject may be any human or non-human animal subject, e.g. any mammalian subject, but will typically be a human subject, or patient.

By "use together" it is meant that the two therapeutically active agents (that is the CFTR modulator and the alginate oligomer) are used in combination to achieve the therapeutic effect. It is particularly meant that a pharmaceutically effective amount of the alginate oligomer is administered at the same or substantially the same time as or prior to administering a pharmaceutically effective amount of the CFTR modulator. In other embodiments the oligomer is administered separately to and after the CFTR modulator. The skilled man would readily be able to design a dosage regimen to maximise the effect of the alginate oligomer and CFTR modulator that are being used in the treatment of a condition arising from or associated with CFTR dysfunction. He would also be able to select optimal combinations of the two active agents depending on the particular clinical situation he is faced with. "Use together" does not imply that the respective agents are present in the same formulation or composition, and accordingly even if used, or administered, at the same or substantially the same time, the alginate oligomer and CFTR modulator need not be present in the same composition or formulation, but may be administered separately. Thus "separate" use/administration includes use/administration at the same or substantially the same time, or at different times, e.g. sequentially, or at different time intervals according to the desired dosage or usage regime. "Simultaneous" administration accordingly includes administration of the alginate oligomer and CFTR modulator within the same composition or formulation, or within separate compositions/formulations administered at the same or substantially the same time.

Expressed alternatively the invention further provides the use of an alginate oligomer for the manufacture of a medicament for use together with (or in combination or conjunction with) a CFTR modulator in the treatment of a condition in a subject arising from or associated with CFTR dysfunction.

The medicament may further comprise the CFTR modulator (or CFTR modulators). The medicament may be in the form of a single composition or formulation comprising the alginate oligomer and CFTR modulator(s) or separate compositions or formulations may be prepared and used, each containing the alginate oligomer or the CFTR modulator(s), respectively.

Thus in a more particular aspect the present invention provides the use of an alginate oligomer and at least one CFTR modulator for the manufacture of a medicament for use in the treatment of a condition in a subject arising from or associated with CFTR dysfunction.

As noted above, the CFTR modulator may be applied or administered separately from the alginate oligomer.

Thus a further aspect of the present invention provides a product containing an alginate oligomer and a CFTR modulator (e.g. one or more CFTR modulators) as a combined preparation for separate, simultaneous or sequential use in the treatment of a condition in a subject arising from or associated with CFTR dysfunction.

The product may be viewed as a pharmaceutical product or combination product, or as a kit, comprising the alginate oligomer and CFTR modulator.

The CFTR modulator may thus be applied or administered simultaneously with the alginate oligomer or sequentially. As noted above, in one embodiment the CFTR modulator is administered at the same or substantially the same time as the alginate oligomer, and in another embodiment it is administered after the alginate oligomer or before the alginate oligomer. Thus, in other embodiments the oligomer is administered separately to, either before or after the CFTR modulator. Included within the scope of "substantially the same time" is application or administration of the CFTR modulator immediately or almost immediately before or after the alginate oligomer. The term "almost immediately" may be read as including application or administration within one hour of the previous application or administration, preferably within 30 minutes. However the CFTR modulator may be applied or administered at least 1 hour, at least 3 hours, or at least 6 hours or more after the alginate oligomer. In these embodiments the CFTR modulator can be applied or administered with or without a further application of an alginate oligomer. The alginate oligomer can be applied or administered in a plurality of applications prior to or with the CFTR modulator, including as noted above, an application or administration immediately or almost immediately after the CFTR modulator. In other embodiments the CFTR modulator may conveniently be applied or administered before the alginate oligomer, e.g. at least 1 hour, at least 3 hours, at least 6 hours before the alginate oligomer. In these embodiments the alginate oligomer can be applied or administered with or without a further application of the CFTR modulator. The CFTR modulator can be applied or administered in a plurality of applications prior to or with the alginate oligomer.

Alternatively expressed, in these various aspects of the invention the alginate oligomer and the CFTR modulator may be used for the treatment of a subject with a condition arising from or associated with CFTR dysfunction. As will be described in more detail below, the invention includes the treatment of any complication of such a condition. Accordingly, references herein to treating said condition include the treatment of one or more complications or clinical manifestations associated with the condition.

BRIEF DESCRIPTION OF THE DRAWINGS

FIG. 3 shows the chemical structures of a variety of CFTR modulators.

DETAILED DESCRIPTION

Figure 1:
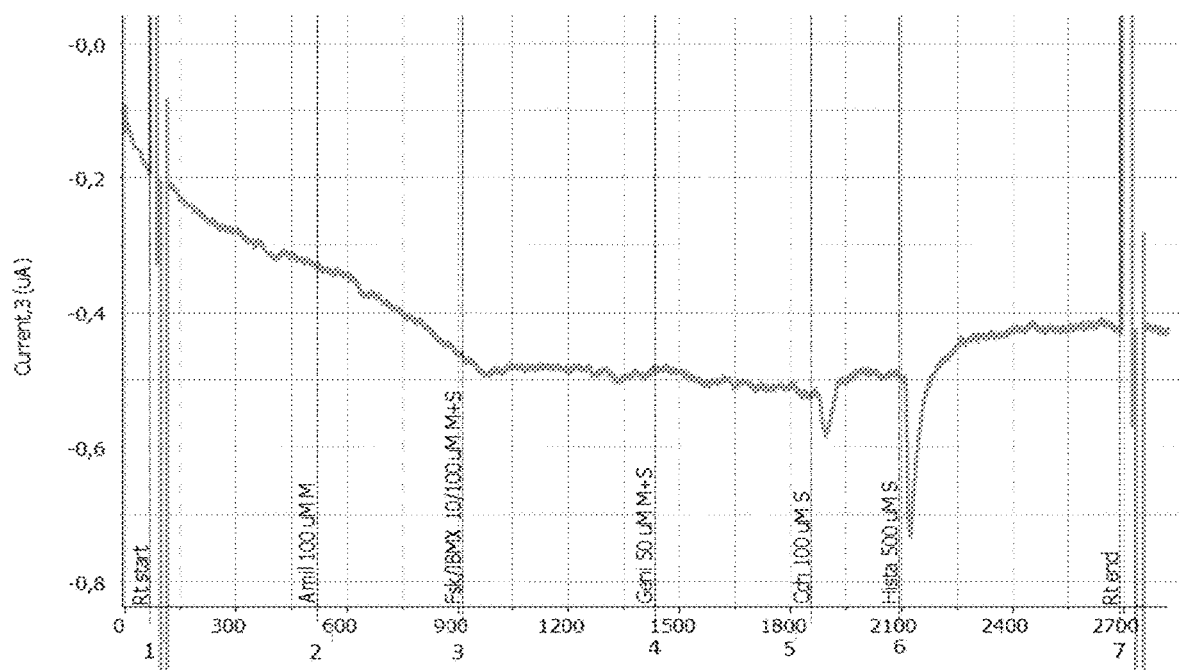
FIG. 1 shows $I_{SC}$ traces measuring CFTR-mediated anion secretion in rectal biopsies from F508del/F508del human patients either as untreated control (A) or pretreated for 18 h with 5 µM VX-809 (M and S) at 37° C. (B).
Figure 1:
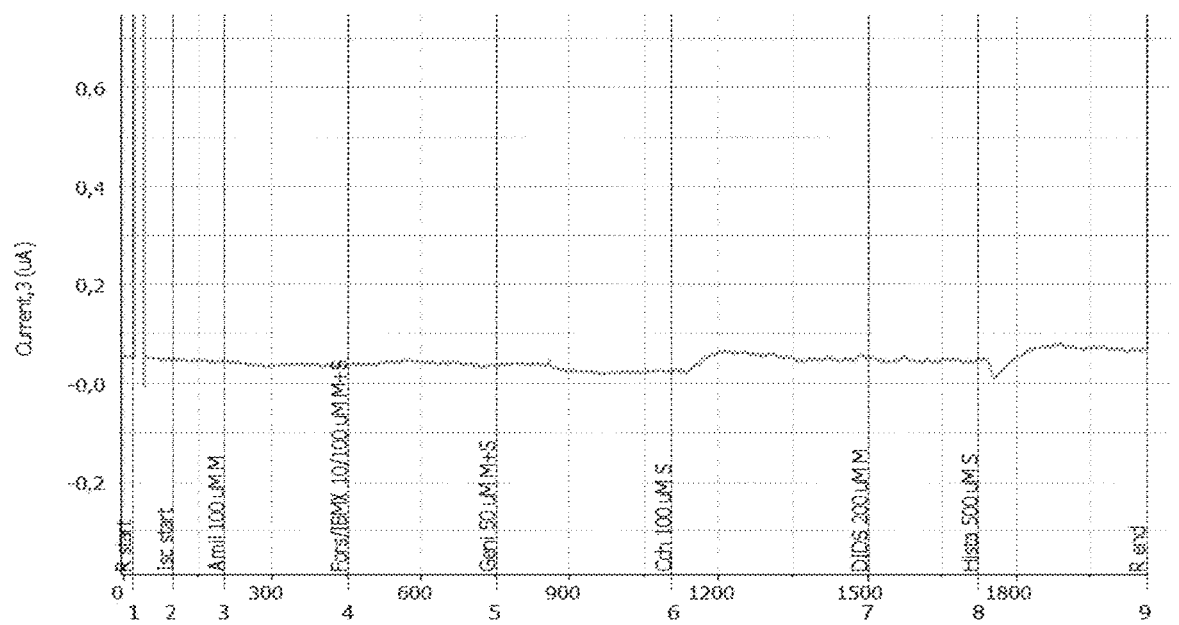

"CFTR dysfunction/CFTR ion channel dysfunction" will be understood to include any defect or deficiency in CFTR ion channel function at a mucosal surface, specifically the epithelial layer of the mucosal surface. This may include CFTR ion channels which are defective in the sense that they are non-functional or have reduced function, i.e. partially or fully lack CFTR ion channel activity (in other words in which CFTR ion channel activity is reduced or abrogated). Thus a lack of functional CFTR ion channels may include a lack of CFTR which are fully functional (i.e. display full or normal CFTR ion channel activity). Also included is the loss or depletion of functional CFTR at the mucosal surface, e.g. as a result of reduced or absent expression of the channel or transport to the epithelial cell surface, or by increased internalisation or turnover or other processing leading to loss/depletion of CFTR ion channels from the epithelial cell surface.

CFTR dysfunction at a mucosal surface may therefore be expressed in terms of reduced CFTR ion channel capacity, more specifically CFTR-mediated ion transport, as compared to normal or healthy mucosal surfaces, in particular a reduction that renders any such transport as insufficient to maintain normal or healthy mucus (thereby giving rise to abnormal mucus). Included in the term "CFTR-mediated ion transport" is the transport of ions through the CFTR itself, and also the transport of ions through secondary mechanisms, e.g. other ion channel proteins at the mucosal surface, that are driven by the ion concentration gradients maintained by the ions transported through the CFTR. Such ions include chloride, sodium and bicarbonate ions.

CFTR dysfunction at a mucosal surface may in turn be caused by any mechanism or combination of mechanisms that decreases the capacity of the population of CFTR at the cell surface to transport ions. This may include the inhibition of ion transport activity of the CFTR at the cell surface, e.g. because of a defect in the protein itself, because of an agent effecting a transient or permanent structural change in protein and/or an agent blocking the ion transport pore/channel. Mechanistically, inhibitory effects can be seen if the pore/channel is blocked to some extent (conductance is decreased) and/or if gating duration or probability (or when considered together "open probability") is decreased. The capacity of the population of CFTR at the cell surface to transport ions may also be decreased if there are too few CFTR at the cell surface. This can occur if expression from the CFTR genes is insufficient. This can also occur if there is a defect in the CFTR gene, transcript or translation product that prevents the CFTR, of a portion of the population thereof, from reaching or inserting correctly into the cell surface. This can also occur if the machinery responsible for CFTR turnover is out of balance in favour of removal (internalisation) rather than replenishment. This latter mechanism may be a result of a defect in the CFTR protein or can be caused by environmental agents. It may also be the case that a subject with CFTR ion channel dysfunction at a mucosal surface has lower than normal numbers of CFTR at the mucosal surface and the CFTR within that population of surface localised CFTR have lower than normal ion transport activity.

Thus, it can be seen that a lack of functional CFTR (e.g. fully functional CFTR) at a mucosal surface, by whatever means, can result in CFTR dysfunction at a mucosal surface and thus insufficient CFTR ion channel capacity to maintain an appropriate ionic balance at the mucosal surface, which is necessary to maintain normal or healthy mucus. It can therefore also been seen that a mucosal surface with CFTR dysfunction will not be able to maintain normal or healthy mucus and thus carries abnormal mucus, in particular mucus which is dense, intractable and in some instances at least partially attached to the underlying epithelium. The properties of this mucus are such that it leads to the pathological conditions disclosed herein and the mucus-related complications thereof, i.e. conditions arising from or associated with CFTR dysfunction.

Thus, the conditions treatable in accordance with the invention may also be described as conditions arising from or associated with abnormal mucus at a mucosal surface displaying CFTR dysfunction. More specifically, the conditions treatable in accordance with the invention may also be described as conditions arising from or associated with abnormal mucus at a mucosal surface with an underlying epithelium displaying CFTR dysfunction.

A mucosal surface is defined herein as any surface of the human body, both internal or external, that secretes, has, carries or is to any extent coated with mucus. More specifically a mucosal surface is a tissue lining comprising epithelial cells, typically arranged as an epithelial cell layer (an epithelium), that secretes, has, carries or is to any extent coated with mucus. It will be recognised that the terms "mucous membrane" and "mucosa" may alternatively be used to refer to a mucosal surface. In accordance with the invention a mucosal surface targeted by the treatments of the invention will be affected by CFTR dysfunction and so will secrete, have, carry or be to any extent coated with the abnormal mucus characteristic of CF (mucus that is dense, intractable and in some instances at least partially attached to the underlying epithelium).

As used herein the term "condition" includes any disease, disorder or condition, whether arising due to a genetic defect or mutation, or in any other way, including an acquired condition, e.g. due to environmental and/or clinical exposure, as discussed above, for example.

In certain embodiments the condition arising from or associated with CFTR dysfunction may be CF, non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD (and its subtypes chronic bronchitis and emphysema), bronchiectasis, asthma and/or chronic sinusitis. More generally the condition may be a respiratory disorder, e.g. an obstructive respiratory disorder. More particularly, in more specific embodiments the condition may be characterised by a chronic inflammatory state, airway remodelling and exacerbations due to respiratory tract infections.

In other embodiments the condition may be a mucus-related complication of the above-listed conditions. In a further specific embodiment the invention provides a treatment for mucus stasis and breathing difficulties in tobacco smokers and other subjects exposed to the chronic inhalation of particulate irritants, e.g. smoke particles (tobacco, wood etc.), pollution, dust (asbestos, cotton, coal, stone, animal droppings etc.) and spores.

Cystic fibrosis is a human disease characterised by mucus and/or exocrine secretions from the lung, pancreas and liver that have abnormal physical properties, typically increased viscosity and, in the case of mucus, adherence to the epithelium of the mucosal surface. These underlying factors manifest in, amongst other conditions, breathing difficulties, respiratory tract infections (chronic and acute, e.g. of the bronchi or of the lungs), respiratory tract inflammation (e.g. bronchial inflammation (termed bronchitis, if due to infection) or pulmonary inflammation/pneumonitis (termed pneumonia, if due to infection)), pulmonary hypertension, heart failure, respiratory failure, lung remodelling, sinus infection, sinusitis (acute, subacute and chronic), facial pain, headaches, abnormal nasal drainage, thickened faeces, constipation, bowel obstruction, nutrient malabsorption, pancreatic inflammation, pancreatitis, diabetes, gallstones, liver cirrhosis, and infertility. Decreased response to antibiotics, especially in the lungs, is also seen. The abnormal mucus and exocrine secretions arise from mutations in CFTR which affect the ability of this protein to transport chloride and bicarbonate ions across epithelial membranes and thereby regulate the balance of other ions such as sodium. Many such mutations of CFTR have been identified, some resulting in a more pronounced CF phenotype than others. A subject can therefore be considered to be suffering from CF if the subject has one or more, preferably 2, 3, 4, 5, 6 or more or all of the above mentioned conditions, abnormal mucus (e.g. dense, intractable mucus which, in some instances may be attached to epithelium at at least one mucosal surface), hyperviscous sputum or other secretions and/or exocrine secretions and a mutation in each of his/her CFTR genes.

Conveniently CF may be diagnosed by the "sweat test". This is a routine test familiar to the person skilled in the art. Briefly, pilocarpine is placed on the skin and uptake induced by electric current. Sweat released at the treatment site in response to the pilocarpine is collected (e.g. absorbed onto a piece of filter paper) and is then analysed for its salt content. A person with CF will have salt concentrations that are one-and-one-half to two times greater than normal. More specifically, for infants up to and including 6 months of age, a chloride level of equal to or less than 29 mmol/L means CF is very unlikely; levels of 30-59 mmol/L mean that CF is possible; and levels greater than or equal to 60 mmol/L mean CF is likely. For people older than 6 months of age, a chloride level of equal to or less than 39 mmol/L means CF is very unlikely; levels of 40-59 mmol/L mean that CF is possible; and levels greater than or equal to 60 mmol/L mean CF is likely.

In accordance with the invention an infant subject (6 months old or younger) to which the treatment of the invention will be applied will have a sweat chloride level of greater than 25 mmol/L, preferably greater than 29 mmol/L, 35 mmol/L, 40 mmol/L, 45 mmol/L, 50 mmol/L, 55 mmol/L or 60 mmol/L and all other patients will have a sweat chloride level of greater than 35 mmol/L, preferably greater than 39 mmol/L, 45 mmol/L, 50 mmol/L, 55 mmol/L or 60 mmol/L.

As discussed above CFTR dysfunction has been recognised as being an underlying factor in conditions other than CF. Such dysfunction may be inherited through the inheritance of one mutated CFTR allele or may be acquired through, for example, chronic inhalation of particulates (in particular tobacco and wood smoke) and the chronic inflammation of the respiratory tract (e.g. in COPD and its subtypes CB and emphysema, bronchiectasis and chronic sinusitis).

Non-compound CFTR gene mutation heterozygosity is a clinical condition in which a subject has one CFTR allele that does not carry a mutation which effects the intracellular processing and/or cell surface ion channel activity of the protein expressed therefrom and one allele that does have a mutation that is detrimental to the intracellular processing and/or cell surface ion channel activity of the protein expressed therefrom. Such subjects do not display overt CF as defined above in so far as several of the various complications of CF are clearly seen at any one time, but heterozygous subjects will have, at least at times, a mild form of the abnormal mucus which characterises CF and so may present with mild forms of one or of the complications of CF without being sufficient severe as prompting a clear diagnosis of CF. Specifically subjects with CFTR heterozygosity have been observed as having recurrent "idiopathic" pancreatitis, congenital bilateral absence of the vas deferens, chronic sinusitis, and idiopathic bronchiectasis, but such patients may present with any of the CF complications described herein.

The CF sweat test can be used to identify patients with suspected non-compound CFTR gene mutation heterozygosity as such patients will fall between the "very unlikely" and "likely" ranges of sweat chloride levels. For an infant patient (6 months old or younger) this may be a sweat chloride level of greater than 25 mmol/L, preferably greater than 29 mmol/L, 35 mmol/L, 40 mmol/L, 45 mmol/L, 50 mmol/L, 55 mmol/L, but less than 60 mmol/L and all other patients will have a sweat chloride level of greater than 35 mmol/L, preferably greater than 39 mmol/L, 45 mmol/L, 50 mmol/L, 55 mmol/L, but less than 60 mmol/L. Genetic testing of suspected patients can then confirm the diagnosis.

CFTR dysfunction can also be assessed directly by performing intestinal current measurements (ICM) on rectal biopsies or nasal potential difference (NPD) measurements in vivo, as described in the literature (e.g. De Boeck, K., et al, Journal or Cystic Fibrosis, 2011, Vol 10 (Suppl 2), S53-S66). Comparison of the results from test subjects to those from normal subject controls provides an indication of CFTR dysfunction. As described more specifically in the Examples, sequential exposure of rectal biopsies to the ion channel modulators indomethacin, amiloride, forskolin/ IBMX, genistein, carbachol and histamine allows the isolation of CFTR activity during ICM.

COPD, also referred to as chronic obstructive lung disease (COLD), and chronic obstructive airway disease (COAD) is a collective term for chronic obstructive lung diseases characterised by chronic inflammation of the airways without dilation, chronically poor airflow and enhanced sputum production. It is generally accepted that the conditions of chronic bronchitis (inflammation of the mucous membranes of the bronchi) and emphysema (breakdown of the lung tissue, specifically the alveoli) are subtypes of COPD. COPD is usually diagnosed as chronically poor lung function that is not improved by administration of bronchodilators and a chronic productive cough. Imaging of the chest, e.g. with MRI and high resolution computerised tomography (HRCT) may also reveal physiologies characteristic of COPD and to rule out other respiratory conditions.

Presently COPD is not reversible and patients deteriorate over time, ultimately succumbing to respiratory failure. The enhanced sputum production observed in COPD and its similar characteristics to CF mucus mean the respiratory complications observed in CF as discussed above are common in COPD patients, in particular the complications linked to infection of the airways.

Bronchiectasis is a disease characterised by chronic enlargement and subsequent breakdown of the bronchi as a result of an inflammatory response, chronically poor lung function that may improve by administration of bronchodilators and a chronic productive cough. Diagnosis is usually based on lung function tests and imaging of the chest, e.g. with MRI and high resolution computerised tomography (HRCT) to reveal the enlarged bronchi characteristic of the disease.

Presently bronchiectasis is not reversible and patients deteriorate over time, ultimately succumbing to respiratory failure. The enhanced sputum production observed in bronchiectasis and its similar characteristics to CF mucus mean the respiratory complications observed in CF as discussed above are common in bronchiectasis patients, in particular the complications linked to infection of the airways.

Chronic sinusitis is the long term, more than three months, inflammation of the paranasal sinuses. The cause of that inflammation may be infection, allergy (usually to particulates including dust, pollution, pollen, spores and microorganisms) or an autoimmune response. The inflammation leads to increased mucus production and impaired sinus drainage and secondary bacterial infections, which further contribute to the inflammatory response. That the sinus mucus of a patient with chronic sinusitis has similar characteristics to CF mucus means the respiratory, and especially the paranasal sinus, complications observed in CF as discussed above are common in patients with chronic sinusitis. A diagnosis of chronic sinusitis is usually confirmed with nasal endoscopy.

Asthma is a chronic airway disease that manifests as acute episodes of air flow obstruction due to transient bronchoconstriction resulting from the tightening of smooth muscle surrounding the airways, predominantly the bronchioles. Such exacerbations are often triggered by exposure to external stimuli. Bronchial inflammation also leads to tissue swelling and oedema thus causing further obstruction. Underlying the overt episodes of bronchoconstriction and airway obstruction are chronic symptoms of airway thickening and remodelling due to scarring and inflammation and overdeveloped mucus glands.

There is currently no cure for asthma and treatment is limited to control of the acute symptoms. The chronic inflammatory processes and tissue remodelling of the airways associated with asthma long term, including enhanced sputum production, mean the respiratory complications observed in CF as discussed above may be seen in asthma patients, in particular the complications linked to infection of the airways.

It has also been recognised that inhalation of particulate irritants, e.g. smoke particles (tobacco, wood etc.), pollution, dust (asbestos, cotton, coal, stone, animal droppings etc.) and spores can result in defective CFTR ion channel function (and thereby CFTR dysfunction) through the inhibition of CFTR ion transport activity and/or through promoting the internalisation of CFTR from epithelial cell surfaces. Over prolonged periods of exposure this can lead to the formation of mucus characteristic of CF and thus abnormal mucus clearance and/or breathing difficulties in subjects who do not present with overt symptoms of a chronic inflammatory respiratory disorder. The abnormal mucus clearance (or mucus stasis) seen in such subjects mean the respiratory complications observed in CF as discussed above are common in such subjects, e.g. smokers, in particular the complications linked to infection and inflammation of the airways.

Accordingly, in certain embodiments the methods of the invention will further comprise a preceding step in which it is determined that the subject has CFTR ion channel dysfunction at one or more mucosal surfaces of the subject. Such a step may comprise the sweat test, ICM or NPD measurements described above and/or a mucus sample from the subject may be assessed for abnormalities, e.g. elevated viscosity and/or the attachment of mucus to the epithelium of one or more mucosal surfaces. In other embodiments the methods of the invention will further comprise a preceding step in which it is determined that the subject has a condition arising from or associated with a CFTR ion channel dysfunction. In more specific embodiments, the methods of the invention will further comprise a preceding step in which it is determined that the subject has cystic fibrosis, non-compound CFTR gene mutation heterozygosity, COPD, CB, emphysema, bronchiectasis, asthma and/or chronic sinusitis.

In the case of CF and non-compound CFTR gene mutation heterozygosity, this may for example be by conducting a sweat test, ICM or NPD measurements, and/or by genetic testing (i.e. by testing for the presence of a mutant CFTR gene, e.g. screening the nucleotide sequences of the patient's CFTR alleles) in combination with the observation and assessment of clinical indicators of CF (in particular mucus viscosity and/or attachment of mucus to the epithelium of mucosal surfaces) and compiling a medical history. In the case of COPD, CB, emphysema, asthma and bronchiectasis this may for example be by measuring lung function with and without bronchodilators, chest imaging and compiling a medical history. In the case of chronic sinusitis this may be by nasal endoscopy and compiling a medical history.

It may be that some of these abovementioned steps are performed to rule out a diagnosis. For instance, a method of the invention may be a method to treat COPD, but this would not necessarily exclude a step in which a subject is assessed for the indicators of CF or a CFTR mutation. Thus, the methods of the invention may further include a preceding step in which it is determined that the subject does not have cystic fibrosis, non-compound CFTR gene mutation heterozygosity, COPD, CB, emphysema, bronchiectasis, asthma and/or chronic sinusitis.

In other embodiments the methods of the invention will further comprise a following step in which the subject's clinical indictors of the condition arising from or associated with a CFTR ion channel dysfunction are assessed and preferably compared to a corresponding assessment made prior to, or earlier in, said treatment in order to determine any changes therein. In more specific embodiments, the methods of the invention will further comprise a following step in which the subject's clinical indictors of CF, non-compound CFTR gene mutation heterozygosity, COPD, CB, emphysema, bronchiectasis, asthma and/or chronic sinusitis (including with respect to the various conditions or complications associated with CF, non-compound CFTR gene mutation heterozygosity, COPD, CB, emphysema, bronchiectasis, asthma and/or chronic sinusitis described above), as appropriate, are assessed and preferably compared to a corresponding assessment made prior to, or earlier in, said treatment in order to determine any changes therein. Parameters relating to the clinical status of a patient with a condition arising from or associated with a CFTR ion channel dysfunction, e.g. a CF patient and patients with non-compound CFTR gene mutation heterozygosity, COPD, CB, emphysema, bronchiectasis, asthma and/or chronic sinusitis, are well known in the art and may be monitored according to known procedures, e.g. in relation to lung performance, lung physiology and measurable signs of inflammation. However, also assessed may be parameters relating to the effect of the alginate oligomers and CFTR modulators of use in the invention on the mucus and/or secretions in or of the subject, for example viscosity, in particular sputum viscosity, or the attachment of mucus to the epithelium of mucosal surfaces of the subject.

The methods and medical uses of the invention can also be considered to be methods of, or medical uses for, treating the complications (especially the mucus-related complications) of the above described conditions associated with or arising from CFTR dysfunction in an patient with the above described condition, which includes preventing, reducing or delaying the development or onset of further complications of the condition, or reducing the risk of a patient with CFTR dysfunction developing or acquiring further complications of the condition. Specifically, this applies to any of the conditions mentioned or discussed above, e.g. CF, non-compound CFTR gene mutation heterozygosity, abnormal mucus clearance in the respiratory tract and/or breathing difficulties resulting from a chronic particulate inhalation, and/or a chronic inflammatory respiratory disorder, e.g. COPD, CB, emphysema, bronchiectasis, asthma and/or chronic sinusitis.

Such complications may be any of those recited in the following sections. For convenience, in the following such conditions are expressed by reference to CFTR dysfunction-associated conditions, but such terms may be interpreted, where context permits, as a condition (or complication) associated with any of the above-listed conditions, e.g. CF, non-compound CFTR gene mutation heterozygosity, etc. as listed above. Thus, such conditions (complications) may be CFTR dysfunction-associated respiratory tract conditions (e.g. respiratory tract infections, respiratory tract inflammations, breathing difficulties, respiratory failure and lung remodelling), CFTR dysfunction-associated cardiovascular conditions (e.g. pulmonary hypertension and heart failure); CFTR dysfunction-associated paranasal sinus conditions (e.g. paranasal sinus infection, sinusitis facial pain, headaches, abnormal nasal drainage, nasal polyps); CFTR dysfunction-associated GI conditions (e.g. constipation, bowel obstruction (e.g. meconium ileus in neonatal subjects and intussusception and DIOS in older patients), nutrient malabsorption); CFTR dysfunction-associated pancreatic conditions (e.g. pancreatic duct obstruction, nutrient malabsorption, pancreatic inflammation, pancreatitis (acute and chronic), diabetes); CFTR dysfunction-associated hepatic conditions (e.g. bile duct obstruction, gallstones, liver cirrhosis); and CFTR dysfunction-associated infertility.

The present invention is therefore also useful prophylactically, since by combating CFTR dysfunction and restoring a more normal mucus phenotype in a subject with an alginate oligomer and a CFTR modulator, the development of CFTR dysfunction-associated conditions, e.g. infections and/or inflammation (most notably in the respiratory tract, GI tract, pancreas and/or liver) may be avoided (i.e. reduced or prevented).

More generally the invention may be considered to be methods of, or medical uses for, treating the above mentioned CFTR dysfunction-associated conditions. The treatment of CFTR dysfunction-associated pulmonary, GI, pancreatic and hepatic conditions (e.g. those specified above) is preferred.

In preferred embodiments the alginate oligomers and CFTR modulators of the invention are used together in the treatment of chronic and acute infections and/or inflammations in the lower respiratory tract of subjects with a mucosal surface in their respiratory tract that is affected by CFTR dysfunction (for example subjects with CF, or any of the conditions listed above), e.g. in the bronchi or in the lungs, especially chronic infections and/or inflammation. Expressed alternatively, the alginate oligomers and CFTR modulators of the invention are used together in the treatment of bronchitis or pneumonia in such subjects. Such infections/inflammations (e.g. bronchitis or pneumonia) may commonly be caused by *Staphylococcus aureus*, *Haemophilus influenzae*, *Pseudomonas aeruginosa*, *Mycobacterium avium* complex, *Mycobacterium tuberculosis* (the causative agent of pulmonary tuberculosis) and *Aspergillus fumigatus* although the infections/inflammations may be caused by any infectious agent, e.g. by bacteria, fungus, virus and parasites. In addition to those already mentioned, common infectious agents found in the respiratory tract include, but are not limited to, *Chlamydophila pneumonia*, *Bordetella pertussis*, *Mycoplasma pneumonia*, *Moraxella catarrhalis*, *Legionella pneumophila*, *Streptococcus pneumonia*, *Chlamydia psittaci*, *Coxiella burnetti*, rhinovirus, coronavirus, influenza virus, respiratory syncytial virus (RSV), adenovirus, metapneumovirus, parainfluenza virus, *Histoplasma capsulatum*, *Cryptococcus neoformans*, *Pneumocystis jiroveci*, *Coccidioides immitis*, *Toxoplasma gondii*, *Strongyloides stercoralis*, *Ascaris lumbricoides*, and *Plasmodium malariae*.

In further preferred embodiments the alginate oligomers and CFTR modulators of the invention may be used together in the treatment of chronic and acute infections and/or inflammations in the upper respiratory tract of subjects with a mucosal surface in their respiratory tract that is affected by CFTR dysfunction (for example subjects with CF or any of the other above-listed conditions), e.g. of the nose, nasal passages, pharynx, larynx and trachea. The treatment of infections and/or inflammations in the trachea of such subjects is especially preferred. Expressed alternatively, the alginate oligomers of the invention may be used to treat rhinitis (inflammation of the nasal mucosa), nasopharyngitis (or rhinopharyngitis; inflammation of the nasal mucosa, pharynx, hypopharynx, uvula, and tonsils), pharyngitis (inflammation of the pharynx, hypopharynx, uvula, and tonsils), epiglottitis (or supraglottitis; inflammation of the superior portion of the larynx and supraglottic area), laryngitis (inflammation of the larynx), laryngotracheitis (inflammation of the larynx, trachea, and subglottic area), tracheitis (inflammation of the trachea and subglottic area) and tonsillitis (inflammation of the tonsils) in such subjects (for example subjects with CF, COPD or any of the other above-listed conditions). These conditions are sometimes collectively termed upper respiratory tract infections and may be caused by any of the infectious agents mentioned above.

The methods and medical uses of the invention can further be considered as methods of, or medical uses for, increasing the responsiveness of a subject with a condition arising from or associated with a CFTR dysfunction, e.g. a subject with CF or any of the other above-listed conditions, especially such a subject with a lung infection, to antimicrobial agents, e.g. the antibiotics, antifungals and antivirals recited below. Responsiveness to an antimicrobial is reference to the effects on an infection observed at the subject level for a particular dose of antimicrobial administered in a particular manner. This includes any sign or symptom of the infection observed at the subject level, e.g. microbial load (total or at a specific location), inflammation, fever, microbial toxin levels and general well-being.

"Treatment" when used in relation to the treatment of a condition arising from or associated with CFTR dysfunction in accordance with the invention is used broadly herein to include any therapeutic effect, i.e. any beneficial effect on said condition or symptom or indicator thereof. Such conditions include not only CF, non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD, CB, emphysema, bronchiectasis, asthma and/or chronic sinusitis, but also conditions or disorders associated with any of these conditions. In this section a reference to a condition or disorder associated with CF, non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD, CB, emphysema, bronchiectasis, asthma and/or chronic sinusitis is interchangeable with a reference to a complication of CF, non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD, CB, emphysema, bronchiectasis, asthma and/or chronic sinusitis.

Specifically in the context of CF and non-compound CFTR gene mutation heterozygosity, because these diseases are genetic diseases which are characterised in each subject by the unique collection of CF- and non-compound CFTR gene mutation heterozygosity-associated disorders and conditions displayed by the subject at the time of receiving the treatments of the invention, the terms "treatment of CF" and "treatment of non-compound CFTR gene mutation heterozygosity" can be considered to be the treatment of any or all of the disorders and conditions of the subject or the treatment of a subset thereof.

Thus, although the invention does not address correction of the underlying genetic defect of CF or non-compound CFTR gene mutation heterozygosity, it relates to treatment of the effects in the body which arise from the defect, e.g. an alleviation of the effects thereof, e.g. effects arising from the abnormal mucus, and includes the treatment of an associated disorder or condition and also an improvement in the clinical effects of the disorder or condition or overall well-being of the subject. In this context, a "cure" of CF or non-compound CFTR gene mutation heterozygosity would amount to complete alleviation of the various CF- or non-compound CFTR gene mutation heterozygosity-associated disorders and conditions displayed by the subject at the time of receiving the treatments of the invention; however the genetic basis for the disease (the CFTR mutation) would still remain. Nonetheless, the invention does not require such a "cure" and as noted above, includes an improvement in any effect which the CF or non-compound CFTR gene mutation heterozygosity has on the body. Thus included, for example, is an improvement in any symptom or sign of a CF- or non-compound CFTR gene mutation heterozygosity-associated disorder or condition, or in any clinically accepted indicator of a CF- or non-compound CFTR gene mutation heterozygosity-associated disorder or condition in the subject (for example, increasing mucociliary clearance in the lungs, reduced incidence of constipation, improvement in nutrient absorption and increased bioavailability of pharmaceuticals and nutritional or digestive enzyme supplements, which in specific embodiments may be seen as increased responsiveness of lung infections to antibiotics and improved digestive health). In the presently claimed treatments it may be that a pre-existing CF- or non-compound CFTR gene mutation heterozygosity-associated disorder or condition is not fully eradicated or the onset of a new CF- or non-compound CFTR gene mutation heterozygosity-associated disorder or condition is not completely halted, but the treatments are sufficient to inhibit these processes to such an extent that the target CF- or non-compound CFTR gene mutation heterozygosity-associated disorder or condition is fully resolved, or at least resolved to some extent, preferably to an extent acceptable to the subject. Treatment thus includes both curative and palliative therapy, e.g. of a pre-existing or diagnosed CF- or non-compound CFTR gene mutation heterozygosity-associated disorder or condition, i.e. a reactionary treatment.

Specifically in the context of conditions associated with or arising from acquired CFTR dysfunction treatment not only includes eradication or elimination of the condition, or cure of the subject, but also an improvement in the condition. Thus included for example, is an improvement in any symptom or sign of the condition, or in any clinically accepted indicator of the condition. Such improvements may be, for example, increased mucociliary clearance in the lungs, reduced incidence of constipation, improvement in nutrient absorption, and increased bioavailability of pharmaceuticals and nutritional or digestive enzyme supplements, which in specific embodiments may be seen as increased responsiveness of lung infections to antibiotics and improved digestive health. Treatment thus includes both curative and palliative therapy, e.g. of a pre-existing or diagnosed condition, i.e. a reactionary treatment.

"Prevention", when used in relation to the treatment of a condition arising from or associated with CFTR dysfunction in accordance with the invention, is used broadly herein to include any prophylactic or preventative effect in the subject against said condition. Such conditions include not only CF, non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD, CB, emphysema, bronchiectasis, asthma and/or chronic sinusitis, but also conditions or disorders associated therewith. In this section a reference to a condition or disorder associated with CF, non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD, CB, emphysema, bronchiectasis, asthma and/or chronic sinusitis is interchangeable with a reference to a complication of CF or any said condition. "Prevention" thus, in general terms, includes delaying, limiting, reducing or preventing an effect of said condition or complication, or one or more symptoms or indications thereof, in a patient or the onset of said condition or complication, or one or more symptoms or indications thereof, for example relative to the condition, complication, symptom or indication thereof prior to the prophylactic treatment.

It will be understood of course that CF and non-compound CFTR gene mutation heterozygosity in the sense of the underlying genetic defect cannot be prevented by the present invention and this is not included. "Prevention" in these contexts thus relates to preventing an effect in the body which arises as a result of the underlying genetic defect, or as a result of the abnormal mucus.

Specifically in the context of CF and non-compound CFTR gene mutation heterozygosity, because these diseases are genetic diseases which are characterised in each subject by the unique collection of CF- or non-compound CFTR gene mutation heterozygosity-associated disorders and conditions displayed by the subject at the time of receiving the treatments of the invention, the term "prevention of CF or non-compound CFTR gene mutation heterozygosity or a CF- or non-compound CFTR gene mutation heterozygosity-associated disorder or condition" can be considered to be the prevention of any CF- or non-compound CFTR gene mutation heterozygosity-associated disorder or condition that the subject has yet to acquire or which the subject has acquired previously but has overcome prior to receiving the claimed treatments.

Prophylaxis explicitly includes both absolute prevention of occurrence or development of an effect of a condition arising from or associated with CFTR ion channel dysfunction, as defined above, or symptom or indication thereof, and any delay in the onset or development of an effect of a condition arising from or associated with a CFTR dysfunction, as defined above, or symptom or indication thereof, or reduction or limitation of the development or progression of a condition arising from or associated with CFTR dysfunction, as defined above, or symptom or indication thereof. The preventative treatments can also be considered as treatments that reduce the risk of a patient acquiring or developing a condition arising from or associated with CFTR dysfunction, as defined above, or symptom or indication thereof.

An "effective amount" of the alginate oligomer and the CFTR modulator is that amount of alginate oligomer and that amount of CFTR modulator that together (or in combination or conjunction) provide measurable treatment of one or more of the conditions arising from or associated with CFTR dysfunction disclosed herein in the subject. More specifically this may be considered that amount of alginate oligomer and that amount of CFTR modulator that together (or in combination or conjunction) provide a measurable reduction, reversal or limitation in CFTR dysfunction at a mucosal membrane of the patient, or a measurable increase in CFTR ion channel capacity at a mucosal surface of the patient and/or a measurable reduction in, limitation of, or reversal of the abnormalities of a mucus layer with CFTR dysfunction in a patient.

The terms "subject with CF", subject suffering from CF", "subject having CF" and "CF subject" are considered to be equivalent and are used interchangeably herein. Corresponding terms directed to any of the other conditions arising from or associated with a defective CFTR ion channel and/or the abnormal mucus which is attached to underlying epithelium mentioned herein are used similarly.

The subject may be of any age, e.g. may be a new-born, an infant, a child, a juvenile, an adolescent or an adult. In certain embodiments the subject has a well-established CFTR dysfunction phenotype which includes symptoms of the condition to be treated in accordance with the invention (e.g. one including chronic infection, chronic inflammation and/or airway remodelling). Experience within the scientific community would suggest that such subjects are less likely to respond to CFTR modulators due to the formation of a complex pathological state within the mucus at the affected mucosal surfaces which acts as a physical and/or functional barrier to the beneficial effects of CFTR modulators. Without wishing to be bound by theory it is believed that by using alginate oligomers together with CFTR modulators a partial reversal of that pathological phenotype within the mucus to a more normal phenotype occurs (i.e. there is a transition of the abnormal mucus to a more normal state) and this provides the CFTR modulators time and/or access to work to reverse the effects of the underlying defect in CFTR function. By "well-established" it is meant that the phenotype has been observed in the subject for at least 2 years, e.g. at least 3, 4, 5, 6, 7, 8, 9 or 10 years. Expressed differently, the subject is at least 5 years old, e.g. at least 6, 7, 8, 9, 10, 11, 12, 13, 14, 15, 16, 17 or 18 years old. The subject is preferably an adolescent or an adult. These latter embodiments apply in particular to subjects with CF or non-compound CFTR gene mutation heterozygosity.

As noted above, alginates typically occur as polymers of an average molecular mass of at least 35,000 Daltons, i.e. approximately 175 to approximately 190 monomer residues, although typically much higher and an alginate oligomer according to the present invention may be defined as a material obtained by fractionation (i.e. size reduction) of an alginate polymer, commonly a naturally occurring alginate. An alginate oligomer can be considered to be an alginate of an average molecular weight of less than 35,000 Daltons (i.e. less than approximately 190 or less than approximately 175 monomer residues), in particular an alginate of an average molecular weight of less than 30,000 Daltons (i.e. less than approximately 175 or less than approximately 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more units or residues and an alginate oligomer for use according to the invention will typically contain 2 to 100 monomer residues, more typically 3, 4, 5 or 6 to 100, and may contain 2, 3, 4, 5 or 6 to 75, 2, 3, 4, 5 or 6 to 50, 2, 3, 4, 5 or 6 to 40, 2, 3, 4, 5 or 6 to 35 or 2, 3, 4, 5 or 6 to 30 residues. Thus, an alginate oligomer for use according to the invention will typically have an average molecular weight of 350, 550, 700, 900 or 1000 to 20,000 Daltons, 350, 550, 700, 900 or 1000 to 15,000 Daltons, 350, 550, 700, 900 or 1000 to 10,000 Daltons, 350, 550, 700, 900 or 1000 to 8000 Daltons, 350, 550, 700, 900 or 1000 to 7000 Daltons, or 350, 550, 700, 900 or 1000 to 6,000 Daltons.

Alternatively put, the alginate oligomer may have a degree of polymerisation (DP), or a number average degree of polymerisation (DPn) of 2 to 100, preferably 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include any one of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

The alginate oligomer is preferably a linear oligomer.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include alginate oligomers with (e.g. containing) 30 to 70% G (guluronate) residues or 70 to 100% G (guluronate) residues. Thus, a representative alginate oligomer for use according to the present invention may contain at least 70% G residues (i.e. at least 70% of the monomer residues of the alginate oligomer will be G residues).

Preferably at least 50% or 60%, more particularly at least 70% or 75%, even more particularly at least 80, 85, 90, 91, 92, 93, 94, 95, 96, 97, 98 or 99% of the monomer residues are guluronate. In one embodiment the alginate oligomer may be an oligoguluronate (i.e. a homooligomer of G, or 100% G)

In a further preferred embodiment, the above described alginates of the invention have a primary structure wherein the majority of the G residues are in so called G-blocks. Preferably at least 50%, more preferably at least 70 or 75%, and most preferably at least 80, 85, 90, 92 or 95% of the G residues are in G-blocks. A G block is a contiguous sequence of at least two G residues, preferably at least 3 contiguous G residues, more preferably at least 4 or 5 contiguous G residues, most preferably at least 7 contiguous G residues.

In particular at least 90% of the G residues are linked 1-4 to another G residue. More particularly at least 95%, more preferably at least 98%, and most preferably at least 99% of the G residues of the alginate are linked 1-4 to another G residue.

The alginate oligomer of use in the invention is preferably a 3- to 35-mer, more preferably a 3- to 28-mer, in particular a 4- to 25-mer, e.g. a 5- to 20-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons or 2000 to 3000 Daltons or 900 to 3500 Daltons. Other representative alginate oligomers include, as mentioned above, oligomers with 5, 6, 7, 8, 9, 10, 11, 12 or 13 to 50, 45, 40, 35, 28, 25, 22 or 20 residues.

It may be a single compound or it may be a mixture of compounds, e.g. of a range of degrees of polymerization. As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

The alginate oligomer of the invention may have a degree of polymerisation (DP), or a number average degree of polymerisation ($DP_n$), of 3-28, 4-25, 6-22, 8-20 or 10-15, or 5-18 or 7-15 or 8-12, especially 10.

The alginate oligomer of the invention may have a degree of polymerisation (DP), or a number average degree of polymerisation ($DP_n$), of 3-24, 4-23, 5-22, 6-21, 7-20, 8-19, 9-18, 10-17, 11-16, 12-15 or 13-14 (e.g. 13 or 14).

The alginate oligomer of the invention may have a degree of polymerisation (DP), or a number average degree of polymerisation (DPn), of 4-25, 5-24, 6-23, 7-22, 8-21, 9-20, 10-19, 11-18, 12-17, 13-16, 14-15 (e.g. 14 or 15).

The alginate oligomer of the invention may have a degree of polymerisation (DP), or a number average degree of polymerisation ($DP_n$), of 5-26, 6-25, 7-24, 8-23, 9-22, 10-21, 11-20, 12-19, 13-18, 14-17 or 15-16 (e.g. 15 or 16).

The alginate oligomer of the invention may have a degree of polymerisation (DP), or a number average degree of polymerisation ($DP_n$), of 4-50, 4-40, 4-35, 4-30, 4-28, 4-26, 4-22, 4-20, 4-18, 4-16 or 4-14.

The alginate oligomer of the invention may have a degree of polymerisation (DP), or a number average degree of polymerisation ($DP_n$), of 5-50, 5-40, 5-25, 5-22, 5-20, 5-18, 5-23, 5-20, 5-18, 5-16 or 5-14.

The alginate oligomer of the invention may have a degree of polymerisation (DP), or a number average degree of polymerisation ($DP_n$), of 6-50, 6-40, 6-35, 6-30, 6-28, 6-26, 6-24, 6-20, 6-19, 6-18, 6-16 or 6-14.

The alginate oligomer of the invention may have a degree of polymerisation (DP), or a number average degree of polymerisation ($DP_n$), of 8-50, 8-40, 8-35, 8-30, 8-28, 8-25, 8-22, 8-20, 8-18, 8-16 or 8-14.

The alginate oligomer of the invention may have a degree of polymerisation (DP), or a number average degree of polymerisation ($DP_n$), of 9-50, 9-40, 9-35, 9-30, 9-28, 9-25, 9-22, 9-20, 9-18, 9-16 or 9-14.

The alginate oligomer of the invention may have a degree of polymerisation (DP), or a number average degree of polymerisation ($DP_n$), of 10-50, 10-40, 10-35, 10-30, 10-28, 10-25, 10-22, 10-20, 10-18, 10-16 or 10-14.

The alginate oligomer of the invention may have a degree of polymerisation (DP), or a number average degree of polymerisation ($DP_n$), of 11-50, 11-40, 11-35, 11-30, 11-28, 11-25, 11-22, 11-20, 11-18, 11-16 or 11-14.

The alginate oligomer of the invention may have a degree of polymerisation (DP), or a number average degree of polymerisation ($DP_n$), of 12-50, 12-40, 12-35, 12-30, 12-28, 12-25, 12-22, 12-20, 12-18, 12-16 or 12-14.

The alginate oligomer of the invention may have a degree of polymerisation (DP), or a number average degree of polymerisation ($DP_n$), of 13-50, 13-40, 13-35, 13-30, 13-28, 13-25, 13-22, 13-20, 13-18, 13-16 or 13-14.

The alginate oligomer of the invention may have a degree of polymerisation (DP), or a number average degree of polymerisation ($DP_n$), of 14-50, 14-40, 14-35, 14-30, 14-28, 14-25, 14-22, 14-20, 14-18, 14-16 or 14-15.

The alginate oligomer of the invention may have a degree of polymerisation (DP), or a number average degree of polymerisation ($DP_n$), of 15-50, 15-40, 15-35, 15-30, 15-28, 15-25, 15-22, 15-20, 15-18 or 15-16.

The alginate oligomer of the invention may have a degree of polymerisation (DP), or a number average degree of polymerisation ($DP_n$), of 18-50, 18-40, 18-35, 18-30, 18-28, 18-25, 18-22 or 18-20.

Preferably the alginate oligomer of the invention is substantially free, preferably essentially free, of alginate oligomers having a degree of polymerisation outside of the ranges disclosed herein. This may be expressed in terms of the molecular weight distribution of the alginate oligomer of the invention, e.g. the percentage of each mole of the alginate oligomer being used in accordance with the invention which has a DP outside the relevant range. The molecular weight distribution is preferably such that no more than 10%, preferably no more than 9, 8, 7, 6, 5, 4, 3, 2, or 1% mole has a DP of three, two or one higher than the relevant upper limit for $DP_n$. Likewise it is preferred that no more than 10%, preferably no more than 9, 8, 7, 6, 5, 4, 3, 2, or 1% mole has a DP below a number three, two or one smaller than the relevant lower limit for $DP_n$.

Suitable alginate oligomers are described in WO2007/039754, WO2007/039760, WO 2008/125828, and WO2009/068841, the disclosures of which are explicitly incorporated by reference herein in their entirety.

Representative suitable alginate oligomers have a $DP_n$ in the range 5 to 30, a guluronate fraction ($F_G$) of at least 0.80, a mannuronate fraction ($F_M$) of no more than 0.20, and at least 95 mole % of DP no more than 25.

Further suitable alginate oligomers have a number average degree of polymerization in the range 7 to 15 (preferably 8 to 12), a guluronate fraction ($F_G$) of at least 0.85 (preferably at least 0.90), a mannuronate fraction ($F_M$) of no more than 0.15 (preferably no more than 0.10), and having at least 95% mole with a degree of polymerization less than 17 (preferably less than 14).

Further suitable alginate oligomers have a number average degree of polymerization in the range 5 to 18 (especially 7 to 15), a guluronate fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17).

Further suitable alginate oligomers have a number average degree of polymerization in the range 5 to 18, a guluronate fraction ($F_G$) of at least 0.92, a mannuronate fraction ($F_M$) of no more than 0.08, and having at least 95% mole with a degree of polymerization less than 20.

Further suitable alginate oligomers have a number average degree of polymerization in the range 5 to 18 (preferably 7 to 15, more preferably 8 to 12, especially about 10), a guluronate fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14).

Further suitable alginate oligomers have a number average degree of polymerization in the range 7 to 15 (preferably 8 to 12), a guluronate fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Further suitable alginate oligomers have a number average degree of polymerization in the range 5 to 18, a guluronate fraction ($F_G$) of at least 0.80, a mannuronate fraction ($F_M$) of no more than 0.20, and having at least 95% mole with a degree of polymerization less than 20.

Further suitable alginate oligomers have a number average degree of polymerization in the range 7 to 15, a guluronate fraction ($F_G$) of at least 0.85, a mannuronate fraction ($F_M$) of no more than 0.15, and having at least 95% mole with a degree of polymerization less than 17.

Further suitable alginate oligomers have a number average degree of polymerization in the range 7 to 15, a guluronate fraction ($F_G$) of at least 0.92, a mannuronate fraction ($F_M$) of no more than 0.08, and having at least 95% mole with a degree of polymerization less than 17.

Further suitable alginate oligomers have a number average degree of polymerization in the range 5 to 20, a guluronate fraction ($F_G$) of at least 0.85 and a mannuronate fraction ($F_M$) of no more than 0.15.

Further suitable alginate oligomers have a number average degree of polymerization about 13 (e.g. 12, 13 or 14), a guluronate fraction ($F_G$) of at least about 0.80, 0.85, 0.87, 0.88, 0.90 or 0.93 (e.g. 0.92, 0.93 or 0.94) and a corresponding mannuronate fraction ($F_M$) of no more than about 0.20, 0.15, 0.13, 0.12, 0.10, or 0.07 (e.g. 0.08, 0.07 or 0.06).

Further suitable alginate oligomers have a number average degree of polymerization about 21 (e.g. 20, 21 or 22), a guluronate fraction ($F_G$) of at least about 0.80 (e.g. 0.85, 0.87, 0.88, 0.90, 0.92, 0.94 or 0.95) and a corresponding mannuronate fraction ($F_M$) of no more than about 0.20 (e.g. 0.15, 0.13, 0.12, 0.10, 0.08, 0.06, 0.05).

Further suitable alginate oligomers have a number average degree of polymerization about 6 (e.g. 5, 6 or 7), a guluronate fraction ($F_G$) of at least about 0.80 (e.g. 0.85, 0.87, 0.88, 0.90, 0.92, 0.94 or 0.95) and a corresponding mannuronate fraction ($F_M$) of no more than about 0.20 (e.g. 0.15, 0.13, 0.12, 0.10, 0.08, 0.06, 0.05).

It will thus be seen that a particular class of alginate oligomers favoured according to the present invention is alginate oligomers defined as so-called "high G" or "G-block" oligomers i.e. having a high content of G residues or G-blocks (e.g. wherein at least 70% of the monomer residues are G, preferably arranged in G-blocks). However, other types of alginate oligomer may also be used, including in particular "high M" or "M-block" oligomers or MG-block oligomers, as described further below. Accordingly, it is alginate oligomers with high proportions of a single monomer type, and with said monomers of this type being present predominantly in contiguous sequences of that monomer type, that represent oligomers that are particularly preferred, e.g. oligomers wherein at least 70% of the monomer residues in the oligomer are G residues linked 1-4 to another G-residue, or more preferably at least 75%, and most preferably at least 80, 85, 90, 92, 93, 94, 95, 96, 97, 98, 99% of the monomers residues of the oligomer are G residues linked 1-4 to another G residue. This 1-4 linkage of two G residues can be alternatively expressed as a guluronic unit bound to an adjacent guluronic unit.

In a further embodiment at least, or more particularly more than, 50% of the monomer residues of the alginate oligomer may be M residues (i.e. mannuronate or mannuronic acid). In other words the alginate oligomer will contain at least or alternatively more than 50% mannuronate (or mannuronic acid) residues. Specific embodiments thus include alginate oligomers with (e.g. containing) 50 to 70% M (mannuronate) residues or e.g. 70 to 100% M (mannuronate) residues. Further specific embodiments also include oligomers containing 71 to 85% M residues or 85 to 100% M residues. Thus, a representative alginate oligomer for use according to this embodiment of the present invention will contain more than 70% M residues (i.e. more than 70% of the monomer residues of the alginate oligomer will be M residues).

In other embodiments at least 50% or 60%, more particularly at least 70% or 75%, even more particularly at least 80, 85, 90, 95 or 99% of the monomer residues are mannuronate. In one embodiment the alginate oligomer may be an oligomannuronate (i.e. a homooligomer of M, or 100% M).

In a further embodiment, the above described alginates of the invention have a primary structure wherein the majority of the M residues are in so called M-blocks. In this embodiment preferably at least 50%, more preferably at least 70 or 75%, and most preferably at least 80, 85, 90 or 95% of the M residues are in M-blocks. An M block is a contiguous sequence of at least two M residues, preferably at least 3 contiguous M residues, more preferably at least 4 or 5 contiguous M residues, most preferably at least 7 contiguous M residues.

In particular, at least 90% of the M residues are linked 1-4 to another M residue. More particularly at least 95%, more preferably at least 98%, and most preferably at least 99% of the M residues of the alginate are linked 1-4 to another M residue.

Other preferred oligomers are alginate oligomers wherein at least 70% of the monomer residues in the oligomer are M residues linked 1-4 to another M-residue, or more preferably at least 75%, and most preferably at least 80, 85, 90, 92, 93, 94, 95, 96, 97, 98, 99% of the monomers residues of the oligomer are M residues linked 1-4 to another M residue. This 1-4 linkage of two M residues can be alternatively expressed as a mannuronic unit bound to an adjacent mannuronic unit.

In a still further embodiment, the alginate oligomers of the invention comprise a sequence of alternating M and G residues. A sequence of at least three, preferably at least four, alternating M and G residues represents an MG block. Preferably the alginate oligomers of the invention comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue. Preferably the MG block is at least 5 or 6 contiguous residues, more preferably at least 7 or 8 contiguous residues.

In a further embodiment the minority uronate in the alginate oligomer (i.e. mannuronate or guluronate) is found predominantly in MG blocks. In this embodiment preferably at least 50%, more preferably at least 70 or 75% and most preferably at least 80, 85, 90 or 95% of the minority uronate monomers in the MG block alginate oligomer are present in MG blocks. In another embodiment the alginate oligomer is arranged such that at least 50%, at least 60%, at least 70%, at least 80%, at least 85%, at least 90%, at least 95%, at least 99%, e.g. 100% of the G and M residues in the oligomer are arranged in MG blocks.

Although at its broadest, the invention extends to embodiments wherein at least 1% but less than 100% of the monomer residues of the oligomer are G residues (i.e. guluronate or guluronic acid), more particularly, and as defined further below, at least 30% of the monomer residues are G residues. Thus, at its broadest the MG block containing alginate oligomer may contain at least 1%, but less than 100%, guluronate (or guluronic acid) residues, but generally the MG block containing alginate oligomer will contain at least 30% (or at least 35, 40 or 45% or 50% G) but less than 100% G. Specific embodiments thus include MG block containing alginate oligomers with (e.g. containing) 1 to 30% G (guluronate) residues, 30 to 70% G (guluronate) residues or 70 to 99% G (guluronate) residues. Thus, a representative MG block containing alginate oligomer for use according to the present invention may contain more than 30%, but less than 70%, G residues (i.e. more than 30%, but less than 70%, of the monomer residues of the MG block alginate oligomer will be G residues).

Preferably more than 30%, more particularly more than 35% or 40%, even more particularly more than 45, 50, 55, 60 or 65%, but in each case less than 70%, of the monomer residues of the MG block containing alginate oligomer are guluronate. Alternatively, less than 70%, more preferably less than 65% or 60%, even more preferably less than 55, 50, 45, 40 or 35%, but in each case more than 30% of the monomer residues of the MG block containing alginate oligomer are guluronate. Any range formed by any combination of these values may be chosen. Therefore for instance the MG block containing alginate oligomer can have e.g. between 35% and 65%, 40% and 60% or 45% and 55% G residues.

In another embodiment the MG block containing alginate oligomer may have approximately equal amounts of G and M residues (e.g. ratios between 65% G/35% M and 35% G/65% M, for instance 60% G/40% M and 40% G/60% M; 55% G/45% M and 45% G/55% M; 53% G/47% M and 47% G/53% M; 51% G/49% M and 49% G/51% M; e.g. about 50% G and about 50% M) and these residues are arranged predominantly, preferably entirely or as completely as possible, in an alternating MG pattern (e.g. at least 50% or at least 60, 70, 80, 85, 90 or 95% or 100% of the M and G residues are in an alternating MG sequence).

In certain embodiments the terminal uronic acid residues of the oligomers of the invention do not have a double bond, especially a double bond situated between the $C_4$ and $C_5$ atom. Such oligomers may be described as having saturated terminal uronic acid residues. The skilled man would be able to prepare oligomers with saturated terminal uronic acid residues without undue burden. This may be through the use of production techniques which yield such oligomers, or by converting (saturating) oligomers produced by processes that yield oligomers with unsaturated terminal uronic acid residues.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion and acid hydrolysis. In one favoured embodiment acid hydrolysis is used to prepare the alginate oligomers on the invention. In other embodiments enzymatic digestion is used with an additional processing step(s) to saturate the terminal uronic acids in the oligomers.

Oligomers may then be separated from the polysaccharide breakdown products chromatographically using an ion exchange resin or by fractionated precipitation or solubilisation or filtration. U.S. Pat. No. 6,121,441 and WO2008/125828, which are explicitly incorporated by reference herein in their entirety, describe a process suitable for preparing the alginate oligomers of use in the invention. Further information and discussion can be found in for example in "Handbooks of Hydrocolloids", Ed. Phillips and Williams, CRC, Boca Raton, Fla., USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from, but not limited to, *Laminaria hyperbora* and *Lessonia nigrescens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii*.

In embodiments where alginate oligomers which have primary structures in which the majority of the G residues are arranged in G-blocks rather than as single residues are required, algal sources are expected to be most suitable on account of the fact that the alginates produced in these organisms tend to have these structures. The bacterial sources may be more suitable for obtaining alginate oligomers of different structures.

The molecular apparatus involved in alginate biosynthesis in *Pseudomonas fluorescens* and *Azotobacter vinelandii* has been cloned and characterised (WO 94/09124; Ertesvåg, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al, Journal of Bacteriology, 2006, Vol 188(15), 5551-5560) and alginates of tailored primary structures can be readily obtained by manipulating these systems.

The G content of alginates (for example an algal source material) can be increased by epimerisation, for example with mannuronan C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azotobacter vinelandii* AlgE epimerases is described in detail in Ertesvåg et al (supra) and Strugala et al (Gums and Stabilisers for the Food Industry, 2004, 12, The Royal Society of Chemistry, 84-94).

To obtain G-block containing alginates or alginate oligomers, epimerisation with one or more *Azotobacter vinelandii* AlgE epimerases other than AlgE4 is preferred as these enzymes are capable of producing G block structures. On the other hand AlgE4 epimerase can be used to create alginates or alginate oligomers with alternating stretches of M/G sequence or primary structures containing single G residue as it has been found that this enzyme seems preferentially to epimerise individual M residues so as to produce single G residues linked to M residues rather than producing G blocks. Particular primary structures can be obtained by using different combinations of these enzymes.

Mutated versions of these enzymes or homologues from other organisms are also specifically contemplated as of use. WO 94/09124 describes recombinant or modified mannuronan C-5 epimerase enzymes (AlgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AlgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure for subsequent alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AlgE genes is disclosed in Gimmestad, M., et al, 2006 (supra).

A further approach is to delete or inactivate the endogenous epimerase genes from an *Azotobacter* or a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer products can be influenced by the culture conditions. It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in a capacity to treat a condition in a human patient arising from or associated with CFTR dysfunction together with (or in combination or conjunction with) a CFTR modulator that is substantially lower than that of the unmodified oligomer. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). The skilled man would be aware of still further chemical modifications that can be made to the monosaccharide subunits of oligosaccharides and these can be applied to the alginate oligomers of the invention.

The invention encompasses the use of a single alginate oligomer or a mixture (multiplicity/plurality) of different alginate oligomers. Thus, for example, a combination of different alginate oligomers (e.g. two or more) may be used.

CFTR modulators are small molecules which can redress, at least partially, a mechanism of CFTR dysfunction from one or more classes of CFTR dysfunction, preferably to the extent that CFTR dysfunction at a mucosal membrane is reduced, limited, or reversed. This may be seen as a reduction in, limitation of, or reversal of the abnormalities of the mucus layer. In preferred embodiments the CFTR modulator converts, at least partially, the abnormal mucus to a normal phenotype, or at least a more normal phenotype (in terms of structure, components and physical properties, e.g. viscosity and attachment to the underlying epithelium). Expressed differently a CFTR modulator will increase CFTR ion channel capacity of a mucosal surface. This may be by increasing the numbers of CFTR ion channels at the mucosal surface and/or by increasing CFTR ion channel activity in the population of CFTR ion channels at the mucosal surface. The increase might not necessarily result in an ion channel capacity equivalent to normal mucosal surfaces, but will be sufficient to result in reduction, limitation or reversal of the abnormalities of the mucus layer. Preferably the CFTR modulator is selected from a CFTR potentiator, a CFTR corrector and a read-through agent.

CFTR potentiators are CFTR modulators which increase the activity of the CFTR ion channel present on the epithelial cell surface (e.g. by increasing the open probability (the gate opening time and/or the gating probability) or conductance of the channel). This may take the form of increasing ion channel activity from a reduced level in a defective CFTR or increasing the ion channel activity above normal levels in a population of normal CFTR of reduced size.

CFTR correctors are CFTR modulators which increase the amount of CFTR protein delivered or retained at the epithelial cell surface. These molecules may achieve this effect in a variety of ways in view of the variety of defects in the processing of CFTR that can cause reduced quantities of CFTR at the epithelial cell surface. For instance, certain CFTR correctors can act as a chaperone facilitating proper folding and post-translational modification of CFTR, protecting CFTR from premature degradation, facilitating intracellular targeting of CFTR and reversing accelerated turnover of CFTR at the cell membrane. This may take the form of increasing the amount of normal CFTR protein delivered or to retained at the epithelial cell surface to levels reflecting healthy cells or increasing the amount of partially defective CFTR protein delivered or to retained at the epithelial cell surface, e.g. to levels greater than that seen with wild type CFTR in healthy cells.

Read-through agents are CFTR modulators which cause the translation machinery of the cell to pass over any premature termination codons in the CFTR mRNA transcript thereby increasing the amount of substantially full length and preferably functional CFTR produced.

In certain embodiments the CFTR modulators is selected from those disclosed in WO2006/002421, WO2007/056341 WO2007134279, WO2009038683, WO2009064959, WO2009073757, WO2009076141, WO2009076142, WO2010019239, WO2010037066, WO2010048526, WO2010053471, WO2010054138, WO2010138484, WO2011019413, WO2011050325, WO2011072241, WO2011127241, WO2011127290, WO2011133751, WO2011133951, WO2011133953, WO2011133956, WO2011146901, Pedemonte, N., et al., J Clin Invest. 2005; 115(9):2564-2571, Van Goor, F. et al., Am J Physiol Lung Cell Mol Physiol 2006, 290: L1117-L1130, and Pedemonte, N., et al., Molecular Pharmacology, 2005 vol. 67 no. 5 1797-1807 the content of which is incorporated herein by reference.

As reported in the art, significant and extensive screening efforts have resulted in the identification of CFTR modulator compounds from a wide range of chemical classes, and also such different types of modulator compound are included within the scope of this invention. Particular mention may be made of potentiators in the phenylglycine, sulphonamide (as reported by Pedemonte et al., Molecular Pharmacology, 2005), pyrazole (e.g. [4-methyl-2-(5-phenyl-1H-pyrazol-3-y)phenol] as reported Van Goor, F. et al, Am J Physiol Lung Cell Mol Physiol 2006), flavone (e.g. the isoflavones and benzoflavones, in particular genistein and apigenin), xanthine (e.g. isobutylmethylxamine (IBMX), 8-cyclopentyl-1,3-dipropylxanthine (CPX), 1-isobutylxanthine (XC-33)), benzothiophene (e.g. tetrahydrobenzothiophene), benzimidazolone (e.g. NS004, 5-trifluoromethyl-1-(5-chloro-2-hydroxyphenyl)1,3-dihydro-2H-benzimi-dazol-2-one;

NS1619, 1,3-dihydro-1-[2-hydroxy-5-(trifluoromethyl)phenyl]-5-(trifluoromethyl)-2H-benzimidazol-2-one), capsaicin, fluorescein (e.g. phloxine B), phenantroline, benzoquinoline, dihydropyridine (e.g. the 1,4-dihydropyridines, in particular felodipine), isoquinoline, and benzo[c]quinolizinium (e.g. MPB-27 (6-hydroxy-7-chlorobenzo[c]quinolizinium), MPB-07 (6-hydroxy-10-chlorobenzo[c]quinolizinium), MPB-91 (5-butyl-10-chloro-6-hydroxybenzo[c] quinolizinium chloride), MPB-104 (5-butyl-7-chloro-6-hydroxybenzo[c]quinolizinium chloride) as reported in Norez et al, J. Pharmacology and Experimental Therapeutics, 2008, 325, 89-99)) classes. Further modulators and corresponding molecular structures of use in the invention are shown in FIG. 3.

Fewer correctors have been identified, but include 4-phenylbutyrate (4-PBA), 1,2,3,4-tetrahydroisoquinoline-3-carboxylic acid diamides, compounds in the isoquinoline, cycloalkylcarboxamido-pyridine benzoic acid and benzo[c] quinolizinium classes (e.g. MPB-07, MPB-80 (10-fluoro-6-hydroxybenzo[c]quinolizinium chloride) MPB-91 and MPB 104) and compounds in various other structural classes as reported by Pedemonte et al. J. Clin. Invest. (2005) and Van Goor, F. et al. Am J Physiol Lung Cell Mol Physiol (2006) and shown in FIG. 3 (aminobenzothiazoles (e.g. 2-aminobenzothiazoles), aminoarylthiazoles (e.g. 2-amino-4-arylthiazoles), quinazolinones (e.g. quinazolinylaminopyrimidones (in particular 2-quinazolinyl-4-aminopyrimidinones), bisaminomethylbithiazoles, N-phenylaminoquinolines (e.g. (N-phenylamino)quinolones)).

Representative CFTR modulators include N-(2,4-di-tert-butyl-5-hydroxyphenyl)-1,4-dihydro-4-oxoquinoline-3-carboxamide (ivacaftor; VX-770), [4-methyl-2-(5-phenyl-1H-pyrazol-3-y)phenol] (VRT-532), VRT-422, 4-cyclohexyloxy-2-{1-[4-(4-methoxy-benzenesulfonyl)-piperazin-1-yl]-ethyl}-quinazoline (VRT-325) (both in Van Goor, F. et al. Am J Physiol Lung Cell Mol Physiol (2006) and FIG. 3), 3-[6-[[1-(2,2-difluoro-1,3-benzodioxol-5-yl)cyclopropanecarbonyl]amino]-3-methylpyridin-2-yl]benzoic acid (lumacaftor; VX-809), VX-661 (tezacaftor; 1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), N6022 (3-[1-(4-carbamoyl-2-methylphenyl)-5-(4-imidazol-1-ylphenyl)pyrrol-2-yl]propanoic acid), ataluren, 1,2,3,4-tetrahydroisoquinoline-3-carboxylic acid diamides, 4-phenylbutyrate (4-PBA), genistein, apigenin, MPB-07, MPB-27, MPB-91, MPB-104, felodipine, NS004, phloxine B, IBMX, CPX, XC-33, capsaicin and gentamicin, preferably ivacaftor, lumacaftor, VX-661, and ataluren and most preferably ivacaftor and lumacaftor.

Of the above mentioned CFTR modulators, the following are considered potentiators: VX-770, VTR-532, genistein, apigenin, MPB-07, MPB-27, MPB-91, MPB-104, felodipine, NS004, phloxine B, IBMX, CPX, XC-33, capsaicin and genistein. Of the above mentioned CFTR modulators, the following are considered correctors: VRT-422, VRT-325, VX-809, VX-661, N6022, 1,2,3,4-tetrahydroisoquinoline-3-carboxylic acid diamides, 4-phenylbutyrate (4-PBA), MPB-07, MPB 80, MPB-91 and MPB-104. Of the above mentioned CFTR modulators, the following are considered read through agents: ataluren and gentamicin.

In certain embodiments the CFTR modulator is not also an antibiotic, in particular an aminoglycoside, e.g. gentamicin. In other embodiments the CFTR modulator is not also an antifungal, an antiviral, an immunostimulatory agent, a growth factor, an enzyme, a physiologically tolerable mucosal viscosity reducing agent (e.g. a mucolytic), an alpha blocker, a bronchodilator, a corticosteroid, an NSAID, a digestive enzyme supplement, an oral antidiabetic drug, an injectable antidiabetic drug.

CFTR modulators may be tested for activity in vivo in any convenient way. For instance by monitoring their effects in the above described sweat test or in a nasal potential difference test. In vitro tests may involve monitoring effects on the ion conductance across the plasma membranes of cells naturally or recombinantly expressing CFTR or defective CFTR or by ICM (as described in De Boeck, K., et al or Example 9). Further assays are described in WO2007056341, the contents of which are incorporated by reference.

Multiple CFTR modulators may be used in accordance with the invention. It may be particularly advantageous to use CFTR modulators from at least two different functional classes selected from the potentiators, the correctors and the read through agents and/or at least two different chemical classes. The skilled man will typically determine the mechanism of CFTR dysfunction at play in his patient before selecting a CFTR modulator(s) to use. The use of ivacaftor together with lumacaftor may be advantageous.

As noted above, in more general terms, the alginate oligomers of the invention may be effective in potentiating the effects of CFTR modulators, e.g. any of those discussed above, or at least may complement their activity. Example 9 lends experimental support in this regard. In particular, and without wishing to be bound by theory, in a certain embodiment it is believed that the alginate oligomers may increase the bioavailability of the CFTR modulator, and in particular its bioavailability at its target site (e.g. a mucosal surface affected by CFTR dysfunction, e.g. in the respiratory tract, GI tract and/or pancreas etc). The alginate oligomers of the invention may therefore be used to increase (or improve) the efficacy (or effectiveness) of CFTR modulators, particularly in redressing CFTR dysfunction at a mucosal surface, converting abnormal mucus to a more normal state, and/or more generally in the treatment of a condition in a subject arising from or associated with CFTR dysfunction. For example the dose of the CFTR modulator being used together with the alginate oligomers of the invention may be lowered as a consequence.

Thus, in another aspect the invention provides a method to improve the efficacy of a CFTR modulator, and in particular the effectiveness (or efficacy) of a CFTR modulator to redress CFTR dysfunction at a mucosal surface, to convert abnormal mucus to a more normal state, or in the treatment of a condition in a human patient arising from or associated with CFTR dysfunction, said method comprising administering the alginate oligomer to a subject together with the CFTR modulator.

Conveniently the CFTR modulator is applied or administered simultaneously with the oligomer or almost immediately before or after the oligomer. However the CFTR modulator may be applied or administered at least 1 hour, at least 3 hours, at least 6 hours after the oligomer. In these embodiments the CFTR modulator can be applied or administered with or without a further application of an alginate oligomer. The oligomer can be applied or administered in a plurality of applications prior to or with the macrolide antibiotic. Other dosing regimens (e.g. where the antibiotic is administered before the oligomer) are described in more detail above and apply mutatis mutandis to this aspect of the invention.

Improving the efficacy of the CFTR modulator includes any aspect of improving or enhancing the effect of the CFTR modulator, e.g. so that the remedial effects of the CFTR modulator on CFTR dysfunction is increased or enhanced in any way over the effect of the CFTR modulator seen in the absence of the alginate oligomer. This may be seen for example in a stronger effect of the CFTR modulator redressing CFTR dysfunction, requiring less CFTR modulator to achieve the same effect seen in the absence of alginate oligomer, or an increased effectiveness seen as increased speed or rate of action, a remedial effect being seen in less time than in the absence of oligomer.

The references to "improving the effectiveness of a CFTR modulator to redress CFTR dysfunction at a mucosal surface or in the treatment of a condition in a subject arising from or associated with CFTR dysfunction" etc. accordingly may include that the alginate oligomer renders the CFTR modulator, at least twice as, or at least four times, at least eight times, at least sixteen times or at least thirty two times more effective at redressing CFTR dysfunction at a mucosal surface, at converting abnormal mucus to a more normal state, or in the treatment of a condition in a subject arising from or associated with CFTR dysfunction. Put in a different way, the oligomer may at least double, at least quadruple, at least octuple, at least sexdecuple or at least duotrigenuple the effectiveness of the CFTR modulator to redress CFTR dysfunction at a mucosal surface, converting abnormal mucus to a more normal state, or in the treatment of a condition in a subject arising from or associated with CFTR dysfunction.

In certain embodiments the effective amount of the alginate oligomer and the effective amount of CFTR modulator are administered in a manner that results in a mucosal surface with CFTR dysfunction being contacted with the alginate oligomer at the same, or substantially the same, time or prior to being contacted with the CFTR modulator. In other words, the doses and/or dosage regime may be such as to deliver (i.e. to result in delivery of) the alginate oligomer and the CFTR modulator to their target site at the same or substantially the same time. The target site may, as noted above, be any mucosal surface affected by CFTR dysfunction. Any clinically acceptable dosing regimen may be used to achieve this. The skilled man would be able to take into account any relevant variable factors (e.g. the routes of administration, the bioavailability, and the pharmacokinetics of the oligomer and the CFTR modulator being used, the subject's physical state, the location of the mucosal surface, etc.) in order to design an appropriate dosing regimen for a particular subject and target conditions.

The mucosal surface may be in the respiratory system, e.g. the upper respiratory tract (nose, nasal passages, pharynx larynx and trachea), the paranasal sinuses and the bronchi (primary, secondary and tertiary) and bronchioles of the lower respiratory tract. Preferably the mucosal surface will be in the respiratory tract, preferably the trachea, bronchi and bronchioles.

Combating CFTR dysfunction at a mucosal surface in the respiratory system and the abnormal mucus associated therewith with an alginate oligomer together with a CFTR modulator is proposed to result in improved mucociliary clearance and improvement in respiratory tract conditions associated with CFTR dysfunction (e.g. respiratory tract infections, respiratory tract inflammations (pneumonia and bronchitis), breathing difficulties, respiratory failure and lung remodelling). The reduction in bacteria and mucus accumulation in the respiratory tract is proposed to reduce or prevent the development of the cardiovascular conditions/cardiovascular complications of CFTR dysfunction or other conditions (e.g. pulmonary hypertension and heart failure).

The treatments of the invention are proposed also to improve paranasal sinus conditions/paranasal sinus complications arising from or associated with CFTR dysfunction (e.g. paranasal sinus infection, sinusitis, facial pain, headaches, abnormal nasal drainage, nasal polyps).

The mucosal surface may be in the gastrointestinal tract, e.g. the mouth, the pharynx, the oesophagus, the duodenum and the small intestine (the jejunum and the ileum). The upper GI tract consists of the mouth, pharynx, oesophagus, stomach, and duodenum, and the lower GI tract, consists of the small intestine, the large intestine (the cecum, the colon and the rectum) and the anus. Combating CFTR dysfunction at a mucosal surface in the GI tract, especially those in the mouth, the pharynx, the oesophagus, the duodenum, and the small intestine (the jejunum and the ileum) and the abnormal mucus associated therewith with an alginate oligomer together with a CFTR modulator is proposed to result in improvement in GI conditions/GI complications arising from or associated with CFTR dysfunction (e.g. constipation, bowel obstruction (e.g. meconium ileus in neonatal subjects and intussusception and DIOS in older patients), nutrient malabsorption).

The mucosal surface may be in the pancreatic and/or bile ducts. Combating CFTR dysfunction at a mucosal surface of the pancreatic and/or bile ducts and the abnormal mucus associated therewith with an alginate oligomer together with a CFTR modulator is proposed to result in improvement in pancreatic conditions/pancreatic complications arising from or associated with CFTR dysfunction (e.g. pancreatic duct obstruction, nutrient malabsorption, pancreatic inflammation, pancreatitis (acute and chronic), and diabetes) and/or hepatic conditions/hepatic complications arising from or associated with CFTR dysfunction (e.g. bile duct obstruction, gallstones and liver cirrhosis).

The mucosal surface may be in the female reproductive system, e.g. the vagina, the cervix, the uterus, the fallopian tubes and the ovaries, preferably the cervix, uterus and the fallopian tubes. The cervix is of particular note. Combating CFTR dysfunction at a mucosal surface of the female reproductive system and the abnormal mucus associated therewith with an alginate oligomer together with a CFTR modulator is proposed to result in improvement in female infertility/female fertility complications arising from or associated with CFTR dysfunction.

The mucosal surface may be in the male reproductive system, e.g. the testes, the epididymis, the vas deferens, the accessory glands, the seminal vesicles, the prostate gland and the bulbourethral gland. The epididymis and the vas deferens are of particular note. Combating CFTR dysfunction at a mucosal surface of the male reproductive system and the abnormal mucus associated therewith with an alginate oligomer together with a CFTR modulator is proposed to result in improvement in male infertility/male fertility complications arising from or associated with CFTR dysfunction.

The alginate oligomers and CFTR modulators of the invention may be administered to the subject in any convenient form or by any convenient means in order to achieve effective amounts at the mucosal surface of the target treatment area, e.g. by topical, enteral (e.g. oral, buccal, sublingual, rectal), parenteral (e.g. intravenous, intrahepatic, intrapancreatic) or by inhalation (including nasal inhalation). Administration may achieve systemic distribution or localised distribution, by which it is meant that delivery is effected to the mucosal surface with CFTR dysfunction (or a region thereof), more specifically the epithelium and the mucus layer of that surface, but essentially no other location in the patient. The skilled person would be able to select an appropriate administration means to suit any particular mucosal surface he/she is seeking to target. In certain embodiments the alginate oligomer may be administered in order to contact the mucus layer primarily and the CFTR modulator may be administered in order to contact the epithelium primarily, but this is not essential and effects of the alginate oligomer on the epithelium and effects of the CFTR modulator on the mucus layer are not ruled out.

In certain preferred embodiments the alginate oligomer and the CFTR modulator are administered via the same route, although not necessarily via the same type of dosage form or in the same dosage form. Nevertheless, there may be instances in which providing the alginate oligomer and the CFTR modulator in the same dosage form or separately but in the same type of dosage form is advantageous. In particular embodiments both the alginate oligomer and the CFTR modulator are administered enterally, e.g. orally or rectally, or by inhalation. Oral or rectal administration is of particular note as it is believed that an enterally administered alginate oligomer may increase the bioavailability of an enterally administered CFTR modulator, e.g. through effects on the mucosal surfaces (specifically the mucus) of the GI tract. The same may apply in the respiratory tract during inhalation therapy with these agents. Consistent with the above discussion, in these embodiments of enteral administration, the alginate oligomer may be administered orally and the CFTR modulator rectally, or vice versa. In other embodiments both the alginate oligomer and the CFTR modulator may be administered orally or rectally.

In certain other embodiments both the alginate oligomer and the CFTR modulator are delivered systemically, e.g. parentally (particularly intravenously), enterally (particularly orally) or by inhalation. In still further embodiments one or other of the alginate oligomer or the CFTR modulator is delivered systemically, e.g. as discussed above, and the other is delivered in a localised manner, e.g. topically, by inhalation or by direct parenteral injection (e.g. intrahepatically or, intrapancreatically). In still further embodiments both the alginate oligomer and the CFTR modulator are delivered in a localised manner, e.g. as discussed above.

Preferably the alginate will be administered by enteral routes or by inhalation, which may be to achieve systemic or localised distribution. Topical administration to parts of the female reproductive system (e.g. the vagina and the cervix) may also be convenient. On the other hand it is common for CFTR modulators to be administered orally or intravenously in order to achieve systemic delivery. Typically this is because localised delivery of a CFTR modulator to a mucosal surface with CFTR dysfunction is perceived to be difficult or poorly effective on account of the need for the CFTR modulator to cross the abnormal mucus of the CFTR dysfunctional mucosal surface in order to reach the epithelial cells carrying or containing the molecular targets of the CFTR modulator.

These issues are acutely felt in the lungs where the abnormal mucus associated with CFTR dysfunction is at its most dense and intractable due to a greater level of bioburden in the respiratory tract (especially the lungs) vis a vis the other mucosal surfaces susceptible to problems caused by CFTR dysfunction. The invention may be advantageous insofar as the alginate oligomers can help transition the abnormal mucus of a mucosal layer with CFTR dysfunction to a more normal phenotype with respect to structure, composition and physical properties and as such use of alginate oligomers alongside CFTR modulators permits, for the first time, the successful localised delivery of CFTR modulators across the abnormal mucus of a mucosal layer with CFTR dysfunction. This is especially the case in the respiratory tract, and in particular the lungs. As such, in certain embodiments at least the CFTR modulator is administered to the target mucosal surface with CFTR dysfunction by inhalation or topically in order to achieve localised delivery. In other embodiments both the alginate oligomer and the CFTR modulator are both delivered by inhalation or topically in order to achieve localised delivery.

These issues are also acutely felt in the context of CFTR potentiators which typically require access to the apical cell membrane of epithelial cells in order to access their biological targets (defective CFTR on the apical cell surface). Thus in further embodiments the CFTR modulator in these treatment contexts is a CFTR potentiator.

The skilled man will be able to formulate the alginate oligomers and CFTR modulators of the invention into pharmaceutical compositions that are adapted for these routes of administration and body distribution according to any of the conventional methods known in the art and widely described in the literature.

More specifically, the alginate oligomers and the CFTR modulators of the invention may be incorporated, separately or together, optionally together with other active agents, with one or more conventional carriers, diluents and/or excipients, to produce conventional galenic preparations such as tablets, pills, granules (e.g. in free form or enclosed in capsules), powders (e.g. inhalable powders, including dry inhalable powders), lozenges, sachets, cachets, elixirs, suspensions, emulsions, solutions, syrups, aerosols (as a solid or in a liquid medium), sprays (e.g. nasal sprays), compositions for use in nebulisers, ointments, creams, salves, soft and hard gelatine capsules, suppositories, pessaries, sterile injectable solutions, sterile packaged powders, and the like. Enteric coated solid or liquid compositions, e.g. enteric coated tablets and enteric coated granules (which may be provided in an enteric-coated capsule or in a non-enteric-coated capsule i.e. in which the coating may or may not be an enteric coating); sterile inhalable and sterile injectable compositions are of particular note.

Examples of suitable carriers, excipients, and diluents are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, and the like. Additional therapeutically active agents may be included in the pharmaceutical compositions, as discussed above in relation to combination therapies above.

Parenterally administrable forms, e.g. solutions suitable for delivery via the intravenous, intrahepatic or intrapancreatic routes mentioned above, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as sterile water for injection, Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975)), which is explicitly incorporated by reference herein in its entirety. The solutions can contain preservatives, antimicrobial agents, buffers and antioxidants conventionally used for parenteral solutions, excipients and other additives which are compatible with the biopolymers and/or CFTR modulators and which will not interfere with the manufacture, storage or use of products.

Simple sterile solutions of alginate oligomers or simple sterile liquid compositions comprising alginate oligomers and/or CFTR modulators may be especially convenient for use during surgical procedures and for delivery to the lungs, e.g. by nebuliser, or to the paranasal sinuses, e.g. by a nasal spray device.

Solid or liquid formulations of the alginate oligomer and/or CFTR modulator may be provided with an enteric coating that prevents degradation in the stomach and/or other parts of the upper GI tract but permits degradation in the lower GI tract, e.g. the small intestine. Such coatings are routinely prepared from polymers including fatty acids, waxes, shellac, plastics, and plant fibres. Specific examples thereof include but are not limited to methyl acrylate-methacrylic acid copolymers, methyl methacrylate-methacrylic acid copolymers, cellulose acetate succinate, hydroxypropyl methylcellulose phthalate, hydroxypropyl methylcellulose acetate succinate (hypromellose acetate succinate), polyvinyl acetate phthalate (PVAP), cellulose acetate trimellitate, and sodium alginate polymer. Enteric coated tablets and enteric coated granules (which may be provided in an enteric-coated capsule or in a non-enteric coated capsule) are of particular note. Enteric coated granules may be prepared in accordance with the teachings of WO 1989008448 and Al-Khedairy, E. B. H, 2006, Iraqi J. Pharm. Sci., Vol. 15 (1) 49, the contents of which are incorporated herein by reference, although the skilled person would be aware of further alternative techniques which may be used.

In certain embodiments tablet forms may have a multi-layered structure, e.g. as disclosed in EP 1681051 and Khan, Z. et al, 2013, BioMed Research International, Vol. 2013, Article ID 569470, the contents of which are incorporated herein by reference, although the skilled person would be aware of further alternative techniques and structures which may be used. Such structures may permit more sophisticated delivery of the active agents contained therein, for instance because the active agent(s) (e.g. the alginate oligomer and/or the CFTR modulator) may be positioned in different layers and/or release rate or barrier substances may be included in one or more layers. By selecting certain layer thicknesses and arrangements (e.g. compositions) the release profile of the active agents contained therein may be tailored. In particular, the release of one or more of the active agents in the multi-layered tablet may be prolonged compared to the release of that active agent from a conventional tablet. In certain embodiments a multi-layered tablet of use in the invention has at least 2, e.g. at least 3, 4, 5, 6, 8 or 10 layers. In these embodiments the multi-layered tablet may also have equal to or less than 10, e.g. equal to or less 8, 6, 5, 4, 3 or 2, layers as appropriate. In certain embodiments the multi-layered tablet of use in the invention has 2, 3, or 4 layers. In these embodiments the multi-layered tablet of use in the invention may contain a CFTR modulator and an alginate oligomer in distinct, e.g. alternating, layers. In certain embodiments a multi-layered tablet contains a CFTR modulator and an alginate oligomer, the alginate oligomer being carried in a layer positioned further toward the outermost surface of the tablet than the part of the tablet carrying the CFTR modulator. Thus, in certain embodiments the multi-layered tablet may be designed to release the alginate oligomer first, before the CFTR modulator.

For topical administration the alginate oligomer and/or CFTR modulator can be incorporated into creams, ointments, gels, salves, transdermal patches and the like. Further topical systems that are envisaged to be suitable are in situ drug delivery systems, for example gels where solid, semi-solid, amorphous or liquid crystalline gel matrices are formed in situ and which may comprise the alginate oligomer (which may be any alginate oligomer as herein defined). Such matrices can conveniently be designed to control the release of the alginate oligomer and/or CFTR modulator from the matrix, e.g. release can be delayed and/or sustained over a chosen period of time. Such systems may form gels only upon contact with biological tissues or fluids, e.g. mucosal surfaces. Typically the gels are bioadhesive and/or mucoadhesive. Delivery to any body site that can retain or be adapted to retain the pre-gel composition can be targeted by such a delivery technique. Such systems are described in WO 2005/023176, which is explicitly incorporated by reference herein in its entirety.

The relative content of the alginate oligomer and/or CFTR modulator in the compositions of the invention can vary depending on the dosage required and the dosage regime being followed but will be sufficient to achieve an effective amount at the mucosal surface of the target treatment area, taking account of variables such as the physical size of the subject to be treated, the nature of the subject's particular ailments, and the location and identity of the target treatment area. The skilled man would know that the amounts of alginate and/or CFTR modulator can be reduced if a multiple dosing regime is followed or increased to minimise the number of administrations or applications.

It has been found that the abnormal mucus at mucosal surfaces with CFTR dysfunction is attached, at least in part, to the underlying epithelium. It has further been found that by administering alginate oligomers in such a way as to achieve a local concentration at at least part of the mucosal surface with CFTR dysfunction of 1% to greater than 6% w/v, e.g. at least 10% w/v, at least partial detachment of the mucus from said mucosal surface can be achieved. This detachment is believed to contribute to the normalisation of the mucus and thus will enhance the advantageous effects of alginate oligomers and CFTR modulators when used together in accordance with the invention. With regard to dosing and dosing forms, the skilled man would be able to prepare suitable dosing forms containing appropriate amounts of alginate oligomer to achieve these local concentrations.

Thus, in certain embodiments the local concentration of the alginate oligomer will be 1 to 10% w/v, 1 to 9% w/v, 1 to 8% w/v, 1 to 7% w/v, 1 to 6% w/v, 5.5% w/v, 1 to 5% w/v, 1 to 4.5% w/v, 1 to 4% w/v, 1 to 3.5% w/v, 1 to 3% w/v, 1 to 2.5% w/v, 1 to 2% w/v or 1 to 1.5% w/v.

In certain embodiments the local concentration of the alginate oligomer will be 1.5 to 10% w/v, 2 to 10% w/v, 2.5 to 10% w/v, 3.5 to 10% w/v, 4 to 10% w/v, 4.5 to 10% w/v, 5 to 10% w/v, 5.5 to 10% w/v, 6 to 10% w/v, 7 to 10% w/v, 8 to 10% w/v, or 9 to 10% w/v.

Any and all combinations of the above mentioned range endpoints are contemplated specifically.

"Local concentration" means the concentration of the administered alginate oligomer that is present at the mucosal surface, or more particularly at the mucus layer or coating, e.g. at the lumen/mucus interface, of the target treatment area (i.e. at at least part of the target mucosal surface). Accordingly, "at the mucosal surface", "at the mucus layer or coating of the mucosal surface" or "at the lumen/mucus interface of the mucosal surface" (which terms are used interchangeably) can be expressed as the "immediate vicinity" of the apical surface of the mucus layer or as "essentially in direct contact" with the apical surface of the mucus layer. Expressed numerically a spatial point less than 1 mm from the apical surface of the mucus layer, e.g. less than 0.5, 0.25, 0.1, 0.05, 0.01, 0.005, 0.001 mm from the apical surface of the mucus layer is at the lumen/mucus interface. In other embodiments the term "local concentration" includes that present within the mucus layer of the mucosal surface at the target treatment area. As mentioned above, it has been shown that the target mucus layer will essentially be fully attached, or partially attached, to the underlying epithelium. The volume under consideration will ultimately be limited by the thickness of the mucus at the target area, which may vary depending on the location of the treatment area, the patient and the severity of their clinical condition, e.g. their CF. In certain embodiments the local concentration is that concentration within the mucus at the lumen/mucus interface. Expressed numerically a spatial point at a depth of less than 1 mm below the apical surface of the mucus layer, e.g. less than 0.5, 0.25, 0.1, 0.05, 0.01, 0.005, 0.001 mm below the apical surface of the mucus layer is at the lumen/mucus interface. In further embodiments local concentration will determined as the concentration (or mean average concentration) present throughout the full depth of the mucus layer at the target treatment area.

"% w/v" (or "percentage weight by volume") is a commonly used expression of the concentration of a solid solute in a liquid or semi-solid solvent. 1% w/v equates to 1 gram of solid per 100 ml of solvent, 2% w/v equates to 2 g of solid per 100 ml of solvent, and so on. Accordingly local concentration may be expressed as g/100 ml, grams per 100 millilitres, g100 ml$^{-1}$. 1% w/v also equates to 10 gram of solid per litre of solvent and so the local concentration range of the present invention can be expressed and 10 g/l to 60 g/l. The skilled man would understand that through appropriate scaling calculations, the local concentration range of the present range can be expressed in terms of any SI unit of mass and volume. Conversion into non-standard measures of concentration is also possible and would be routine to the skilled man.

In the context of the present invention "local concentration" will typically amount to the concentration of the alginate oligomer of the invention in the body fluid present at the lumen/mucus interface of the target mucosal surface, the aqueous outer layer of the mucus (e.g. in the case of the respiratory tract, paranasal sinuses and parts of the reproductive system where an air filled lumen is present), or the topical delivery vehicle if so used. As mentioned above in other embodiments the term "local concentration" also includes that present within the mucus layer of the mucosal surface at the target treatment area.

The relevant volume of the solvent/mucus will be determined in part by the size of the target treatment area under consideration. This may be all or part of the respiratory tract, the GI tract, the pancreatic duct, the bile duct, the paranasal sinuses, e.g. those parts recited below, or a subsection thereof. As mentioned above "at the lumen/mucus interface" of the mucosal surface of the target treatment area means a spatial point less than 1 mm from the apical surface of the mucus layer. Within that volume a sufficient mass of alginate must be present to achieve the effective concentration range.

The skilled man would be able to determine routinely the amount of alginate oligomer he would need to administer to achieve the necessary concentration thereof at the lumen/mucus interface of the mucosal surface at the target treatment area. This amount will vary depending on the location of the target treatment area, the route of administration and dosage form being used and the particular pharmacokinetic factors that are relevant, but the skilled man would be able to consider all the factors and arrive at a suitable dosing regimen. In the case of topical compositions, the composition may simply be formulated to contain the alginate oligomer at the requisite local concentration. Any improvement in any of the symptoms or indicators of the condition being treated in accordance with the invention in a patient (for example CF or any of the other above-mentioned CFTR dysfunction-associated conditions or complications thereof) or any other condition, displayed by the patient, or any prophylactic or preventative effect in such a patient, can be considered indicative that the appropriate local concentration has been achieved.

Local concentration can be measured directly to ensure appropriate dosing. This may be achieved through sample extraction and analysis or by imaging labelled versions of the alginate oligomer. Suitable sample collection techniques will depend on the target treatment area, but in general can include sputum collection (respiratory tract), swabbing (e.g. nose, mouth and throat, lower GI tract and lower female reproductive tract), mucus biopsy and tissue biopsy, e.g. via an endoscopic procedure. Such procedures include esophagogastroduodenoscopy (oesophagus, stomach and duodenum), enteroscopy (small intestine), colonoscopy, (colon), sigmoidoscopy (large intestine) cholangioscopy (bile and pancreatic ducts), rectoscopy (rectum), anoscopy (anus), proctoscopy (anus and rectum), rhinoscopy (nose/sinus), bronchoscopy (lower respiratory tract), otoscopy (ear), cystoscopy (urinary tract), gynoscopy (female reproductive system), colposcopy (cervix), hysteroscopy (uterus), falloposcopy (fallopian tubes), laparoscopy (abdominal or pelvic cavity). Labelled alginate oligomers may be radioactive or luminescent (e.g. fluorescent). The signals emanating from these labelled alginate oligomers can be detected via appropriate means and quantified and then used to calculate local concentration.

A representative topical formulation, e.g. a cream, ointment or salve, which may be used to administer an alginate oligomer of the invention to the cervix or other parts of the lower female reproductive system might contain 1 to 25%, 1 to 20%, 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v of the oligomer, the remainder being comprised of pharmaceutically acceptable excipients, and/or other active agents (e.g. the CFTR modulator) if being used. Delivery devices designed for the application of topical formulations to the female reproductive system are known and may be employed to deliver the above mentioned formulations if convenient.

For administration to the nose or paranasal sinuses a sterile aqueous and/or oil-based liquid formulation (e.g. an emulsion) may be used; administered for instance by a nasal spray device, e.g. propellant-free or propellant-assisted. A representative formulation may contain 1 to 25%, 1 to 20%, e.g. 1 to 15%, 1 to 10%, 1 to 9%, 1 to 8%, 1 to 7% or 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the oligomer, the remainder being comprised of pharmaceutically acceptable excipients, e.g. water, and/or other active agents (e.g. the CFTR modulator) if being used.

In other embodiments a slow, delayed or sustained release formulations may be used for delivery, e.g. to the nose or paranasal sinuses. A representative formulation may be a powder containing the alginate oligomer or a suspension of said powder, said powder containing up to 90%, e.g. up to 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the oligomer, the remainder being comprised of pharmaceutically acceptable excipients and/or other active agents (e.g. the CFTR modulator) if being used. The powder may comprise a coating that controls release of the alginate oligomer A representative inhalable solution to be used to administer an alginate oligomer of the invention to the upper respiratory tract typically will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20% or 15 to 25% w/v of the oligomer, the remainder being comprised of pharmaceutically acceptable excipients, e.g. water, and/or other active agents (e.g. the CFTR modulator) if being used.

A representative inhalable powder to be used to administer an alginate oligomer of the invention to the lower respiratory tract may contain up to 90%, e.g. up to 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the oligomer, the remainder being comprised of pharmaceutically acceptable excipients and/or other active agents (e.g. the CFTR modulator) if being used in the same composition.

A representative tablet to be used to administer an alginate oligomer of the invention to the lower GI tract may contain up to 99%, up to 95%, 90%, 85% or 80%, e.g. 50 to 95%, 55 to 95%, 60 to 95%, 65 to 95%, 70 to 95%, 75 to 95%, 80 to 95%, 85 to 95%, 90 to 95%, 50 to 90%, 50 to 90%, 55 to 90%, 60 to 90%, 65 to 90%, 70 to 90%, 75 to 90%, 80 to 90%, 85 to 90%, 50 to 90%, 55 to 85%, 60 to 80% or, 65 to 75% w/v or w/w of the oligomer, the remainder being comprised of pharmaceutically acceptable excipients and/or other active agents (e.g. the CFTR modulator) if being used. The tablet may be a multi-layered tablet. In such embodiments the CFTR or other active agents, if present, may be in a different layer or internal to the layer(s) carrying the alginate oligomer. Preferably the alginate oligomer is in a layer positioned further toward the outermost surface of the tablet than the part of the tablet carrying the CFTR modulator or other active agent.

An enteric coated tablet may also be effective in administering an alginate oligomer of the invention to the lower GI tract. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres) and/or other active agents (e.g. the CFTR modulator) if being used. The tablet may be a multi-layered tablet, e.g. as described above.

Enteric coated granules may also be effective in administering an alginate oligomer of the invention to the lower GI tract. Such granules may be provided in a capsule which itself may or may not be provided with an enteric coating. A representative enteric coated granule may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres) and/or other active agents (e.g. the CFTR modulator) if being used.

A pessary may be used to administer an alginate oligomer of the invention to the lower parts of the female reproductive tract. A representative formulation may contain 1 to 25%, 1 to 20%, e.g. 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the oligomer, the remainder being comprised of pharmaceutically acceptable excipients, including solid excipients (e.g. paraffin and the like), and/or other active agents (e.g. the CFTR modulator) if being used. Rectal suppositories may be formulated similarly.

A representative aqueous solution for direct delivery to a mucosal surface in the liver, the pancreas or the reproductive system will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20%, or 15 to 25% w/v of the oligomer, the remainder being comprised of water and pharmaceutically acceptable excipients and/or other active agents (e.g. the CFTR modulator) if being used.

The alginate oligomer may be used at a daily dose of 0.1 g to 10 g, e.g. 0.5 g to 5 g, 0.8 g to 3 g, 1 g to 2 g, e.g. about 2 g, which may be administered at one or more times per day (e.g. bis daily) and in one or more dosage forms or administration events (e.g. two tablets bis daily).

A representative oral tablet to be used to administer a CFTR modulator systemically may contain up to 99%, up to 95%, 90%, 85% or 80%, e.g. 50 to 95%, 55 to 95%, 60 to 95%, 65 to 95%, 70 to 95%, 75 to 95%, 80 to 95%, 85 to 95%, 90 to 95%, 50 to 90%, 50 to 90%, 55 to 90%, 60 to 90%, 65 to 90%, 70 to 90%, 75 to 90%, 80 to 90%, 85 to 90%, 50 to 90%, 55 to 85%, 60 to 80% or, 65 to 75% w/v or w/w of the CFTR modulator, the remainder being comprised of pharmaceutically acceptable excipients and/or other active agents (e.g. an alginate oligomer) if being used. The tablet may be a multi-layered tablet. In such embodiments the alginate oligomer or other active agents, if present, may be in a different layer or in a layer positioned further toward the outermost surface of the tablet than the part of the tablet carrying the CFTR modulator.

An enteric coated oral tablet may also be effective in administering a CFTR modulator of the invention to the lower GI tract. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the CFTR modulator, the remainder being comprised of pharmaceutically acceptable excipients, including the enteric coating (e.g. polymers including fatty acids, waxes, shellac, plastics, and plant fibres) and/or other active agents (e.g. an alginate oligomer) if being used. The tablet may be a multi-layered tablet, e.g. as described above.

Enteric coated granules may also be effective in administering a CFTR modulator of the invention to the lower GI tract. Such granules may be provided in a capsule which itself may or may not be provided with an enteric coating. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the CFTR modulator, the remainder being comprised of pharmaceutically acceptable excipients, including the enteric coating (e.g. polymers including fatty acids, waxes, shellac, plastics, and plant fibres) and/or other active agents (e.g. an alginate oligomer) if being used.

A representative powder for oral administration following admixture with food or beverages may contain up to 100%, e.g. up to 99%, 95%, 90%, 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the CFTR modulator, the remainder being comprised of pharmaceutically acceptable excipients and/or other active agents (e.g. an alginate oligomer) if being used in the same composition.

A representative solution for intravenous administration of a CFTR modulator of the invention may contain up to 1 to 25%, 1 to 20%, e.g. 1 to 15%, 1 to 10%, 1 to 9%, 1 to 8%, 1 to 7% or 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the CFTR modulator, the remainder being comprised of pharmaceutically acceptable excipients, e.g. water, and/or other active agents (e.g. an alginate oligomer) if being used.

A representative inhalable solution to be used to administer a CFTR modulator of the invention to the upper respiratory tract typically will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20% or 15 to 25% w/v of the CFTR modulator, the remainder being comprised of pharmaceutically acceptable excipients, e.g. water, and/or other active agents (e.g. an alginate oligomer) if being used.

A representative inhalable powder to be used to administer a CFTR modulator of the invention to the lower respiratory tract may contain up to 90%, e.g. up to 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the CFTR modulator, the remainder being comprised of pharmaceutically acceptable excipients and/or other active agents (e.g. an alginate oligomer) if being used in the same composition.

A representative topical formulation, e.g. a cream, ointment or salve, which may be used to effect localised administration of a CFTR modulator of the invention to the cervix or other parts of the lower female reproductive system might contain 1 to 25%, 1 to 20%, 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v of the CFTR modulator, the remainder being comprised of pharmaceutically acceptable excipients, and/or other active agents (e.g. an alginate oligomer) if being used. Delivery devices designed for the application of topical formulations to the female reproductive system are known and may be employed to deliver the above mentioned formulations if convenient.

A pessary may also be used to effect localised administration of an alginate oligomer of the invention to the lower parts of the female reproductive tract. A representative formulation may contain 1 to 25%, 1 to 20%, e.g. 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the CFTR modulator, the remainder being comprised of pharmaceutically acceptable excipients, including solid excipients (e.g. paraffin and the like), and/or other active agents (e.g. an alginate oligomer) if being used. Rectal suppositories may be formulated similarly.

For localised administration of the CFTR modulator of the invention to the nose or paranasal sinuses a sterile aqueous and/or oil-based liquid formulation (e.g. an emulsion) may be used; administered for instance by a nasal spray device, e.g. propellant-free or propellant-assisted. A representative formulation may contain 1 to 25%, 1 to 20%, e.g. 1 to 15%, 1 to 10%, 1 to 9%, 1 to 8%, 1 to 7% or 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the CFTR modulator, the remainder being comprised of pharmaceutically acceptable excipients, e.g. water, and/or other active agents (e.g. an alginate oligomer) if being used.

In other embodiments a slow, delayed or sustained release formulations may be used for localised delivery of the CFTR modulator, e.g. to the nose or paranasal sinuses. A representative formulation may be a powder containing the CFTR modulator or a suspension of said powder, said powder containing up to 90%, e.g. up to 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the CFTR modulator, the remainder being comprised of pharmaceutically acceptable excipients and/or other active agents (e.g. an alginate oligomer) if being used. The powder may comprise a coating that controls release of the CFTR modulator.

A representative aqueous solution for direct delivery of the CFTR modulator to a mucosal surface in the liver, the pancreas or the reproductive system will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20%, or 15 to 25% w/v of the CFTR modulator, the remainder being comprised of water and pharmaceutically acceptable excipients and/or other active agents (e.g. an alginate oligomer) if being used.

The CFTR modulator may be used at a daily dose of 0.1 mg/kg to 50 mg/kg, preferably 1 mg/kg to 25 mg/kg or 5 mg/kg to 20 mg/kg of subject body weight.

In still further embodiments of the invention the alginate oligomers and CFTR modulators as herein defined may be used in the methods or uses of the invention in conjunction or combination with a further pharmaceutical for the treatment of CF or CF-associated disorders or conditions/complications of CF (hereinafter "further CF pharmaceutical"). Such pharmaceutical may also be considered as being for use, inter alia, in the treatment of non-compound CFTR gene mutation heterozygosity, abnormal mucus clearance in the respiratory tract and/or breathing difficulties resulting from chronic particulate inhalation, and/or a chronic inflammatory respiratory disorder, e.g. COPD, CB, emphysema, bronchiectasis, asthma and/or chronic sinusitis, conditions associated therewith or complications thereof. Such pharmaceutical may also be considered as being for use, inter alia, in the treatment of conditions arising from or associated with CFTR dysfunction.

The further CF pharmaceutical (i.e. further therapeutically active agent) may be an antibiotic, an antifungal, an antiviral, an immunostimulatory agent, a corticosteroid, a non-steroidal anti-inflammatory drug (NSAID), a bronchodilator, a digestive enzyme supplement, an oral antidiabetic drug, an injectable antidiabetic drug, a laxative agent or a mucus viscosity-reducing agent (i.e. an agent which reduces the viscosity of mucus and which terms are used interchangeably with the term "mucolytic agent").

The antibiotic may be selected from the aminoglycosides (e.g. amikacin, gentamicin, kanamycin, neomycin, netilmicin, streptomycin, tobramycin); the β-lactams (e.g. the carbecephems (e.g. loracarbef); the 1st generation cephalosporins (e.g. cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the monobactams (e.g. aztreonam); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the glycylcyclines (e.g. tigecycline); the carbapenems (e.g. imipenem, meropenem, ertapenem, doripenem, panipenem/betamipron, biapenem, PZ-601); other antibiotics include chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

More preferably the antibiotic is selected from amikacin, gentamicin, kanamycin, neomycin, netilmicin, streptomycin, tobramycin, cefixime, cefdinir, cefditoren, cefoperazone, cefotaxime, cefpodoxime, ceftazidime, ceftibuten, ceftizoxime, ceftriaxone, cefepime, aztreonam, amoxicillin, ampicillin, carbenicillin, cloxacillin, dicloxacillin, nafcillin, oxacillin, penicillin G, penicillin V, piperacillin, ticarcillin, ciprofloxacin, enoxacin, gatifloxacin, levofloxacin, lomefloxacin, moxifloxacin, norfloxacin, ofloxacin, trovafloxacin, azithromycin, clarithromycin, dirithromycin, erythromycin, roxithromycin, telithromycin, CarbomycinA, josamycin, kitasamycin, midecamicine, oleandomycin, spiramycin, troleandromycin, tylosin, imipenem, meropenem, ertapenem, doripenem, panipenem/betamipron, biapenem, PZ-601, bacitracin, colistin, polymyxin B, demeclocycline, doxycycline, minocycline, oxytetracycline and tetracycline.

More preferably the antibiotic is selected from aztreonam, ciprofloxacin, gentamicin, tobramycin, amoxicillin, colistin, ceftazidime, azithromycin, clarithromycin, dirithromycin, erythromycin, roxithromycin, spiramycin, oxytetracycline, and imipenem.

In particularly preferred embodiments the antibiotic is selected from aztreonam, ciprofloxacin, gentamicin, tobramycin, amoxicillin, colistin and ceftazidime.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Representative immunostimulatory agents include, but are not limited to cytokines e.g. TNF, IL-1, IL-6, IL-8 and immunostimulatory alginates, such as high M-content alginates as described for example in U.S. Pat. No. 5,169,840, WO91/11205 and WO03/045402 which are explicitly incorporated by reference herein in their entirety, but including any alginate with immunostimulatory properties.

Representative NSAIDs include, but are not limited to, the salicylates (e.g. aspirin (acetylsalicylic acid), choline magnesium trisalicylate, diflunisal, salsalate, the propionic acid derivatives (e.g. ibuprofen, dexibuprofen, dexketoprofen, fenoprofen, flurbiprofen, ketoprofen, loxoprofen, naproxen, oxaprozin), the acetic acid derivatives (e.g. aceclofenac, diclofenac, etodolac, indomethacin, ketorolac, nabumetone, tolmetin, sulindac), the enolic acid derivatives (e.g. droxicam, isoxicam, lornoxicam, meloxicam, piroxicam, tenoxicam), the anthranilic acid derivatives (e.g. flufenamic acid, meclofenamic acid, mefenamic acid, tolfenamic acid) and the selective COX-2 inhibitors (Coxibs; e.g. celecoxib, etoricoxib, lumiracoxib, parecoxib, rofecoxib, valdecoxib). The propionic acid derivatives (e.g. ibuprofen, dexibuprofen, dexketoprofen, fenoprofen, flurbiprofen, ketoprofen, loxoprofen, naproxen, oxaprozin) are preferred, ibuprofen being most preferred.

As used herein, the terms "mucolytic agent" and "mucus viscosity reducing agent" are intended to encompass agents which reduce the intrinsic viscosity of mucus and agents which reduce the attachment of mucus to underlying epithelium, in particular agents which directly or indirectly disrupt the molecular interactions within or between the components of mucus, agents which affect the hydration of mucus and agents which modulate the ionic microenvironment of the mucosal epithelium (particularly the levels of divalent cations, e.g. calcium). Representative examples of suitable mucus viscosity reducing agents include but are not limited to a nucleic acid cleaving enzyme (e.g. a DNase such as DNase I or dornase alfa), hypertonic saline, gelsolin, a thiol reducing agent, an acetylcysteine, an uncharged low molecular weight polysaccharide (e.g. dextran, mannitol), arginine (or other nitric oxide precursors or synthesis stimulators), an agonist of the P2Y2 subtype of purinergic receptors (e.g. denufosol) or an anionic polyamino acid (e.g. poly ASP or poly GLU). Ambroxol, bromhexine, carbocisteine, domiodol, eprazinone, erdosteine, letosteine, mesna, neltenexine, sobrerol, stepronin, tiopronin are specific mucolytics of note. DNase I and hypertonic saline are preferred.

Representative examples of suitable bronchodilators include but are not limited to the β2 agonists (e.g. the short-acting β2 agonists (e.g. pirbuterol, epinephrine, salbutamol, levosalbutamol, clenbuterol, terbutaline, procaterol, metaproterenol, fenoterol, bitolterol mesylate, ritodrine, isoprenaline); the long-acting β2 agonists (e.g. salmeterol, formoterol, bambuterol, clenbuterol); and the ultra-long-acting β2 agonists (e.g. indacaterol)), the anticholinergics (e.g. ipratropium, oxitropium, tiotropium) and theophylline.

Representative examples of suitable corticosteroids include but are not limited to prednisone, flunisolide, triamcinolone, fluticasone, budesonide, mometasone, beclomethasone, amcinonide, budesonide, desonide, fluocinonide, fluocinolone, halcinonide, hydrocortisone, cortisone, tixocortol, prednisolone, methylprednisolone, prednisone, betamethasone, dexamethasone, fluocortolone, aclometasone, prednicarbate, clobetasone, clobetasol, and fluprednidene.

Representative examples of suitable digestive enzyme supplements include but are not limited to pancrelipase (a mixture of pancreatic lipases, amylases, and chymotrypsin), pancreatin (a mixture of pancreatic lipases, amylases, and trypsin) or one or more lipases (e.g. bile salt dependent lipase, pancreatic lipase, gastric lipase, pancreatic lipase related protein 1, pancreatic lipase related protein 2, lingual lipase), proteases (e.g. pepsin, trypsin and chymotrypsin) and amylases (e.g. α-amylase, β-amylase, γ-amylase). These enzymes may be plant enzymes or animal enzymes, including human. These enzymes may be obtained from natural sources or prepared by molecular biology techniques.

Representative examples of suitable oral antidiabetic drugs include, but are not limited to, the sulfonylureas (e.g. carbutamide, acetohexamide, chlorpropamide, tolbutamide, glipizide, gliclazide, glibenclamide, glibornuride, gliquidone, glisoxepide, glyclopyramide, glimepiride), the biguanides (e.g. metformin, phenformin, buformin, proguanil), the thiazolidinediones (e.g. rosiglitazone, pioglitazone, troglitazone), the alpha-glucosidase inhibitors (e.g. acarbose, miglitol, voglibose), the meglitinides (e.g. nateglinide, repaglinide, mitiglinide), and the glycosurics (e.g. dapagliflozin, ganagliflozin, ipragliflozin, tofogliflozin, empagliflozin, sergliflozin etabonate, remogliflozin etabonate).

Representative examples of suitable injectable antidiabetic drugs include, but are not limited to, insulin and its analoges (e.g. insulin lispro, insulin aspart, insulin glulisine, insulin zinc, isophane insulin, insulin glargine, insulin detemir) and the incretin mimetics (e.g. the glucagon-like peptide (GLP) agonists, e.g. exenatide, liraglutide, and taspoglutide; and the dipeptidyl peptidase-4 (DPP-4) inhibitors, e.g. vildagliptin, sitagliptin, saxagliptin, linagliptin, allogliptin and septagliptin).

Representative examples of suitable laxative agents include but are not limited to the bulk-forming laxatives (e.g. ispaghula husk, methylcellulose, ethylhydroxyethylcellulose, gum karaya, linseed fibre, wheat fibre, polycarbophil calcium); osmotic laxatives (e.g. glycerin suppositories, sorbitol, lactitol, mannitol, laminarid, lactulose, polyethylene glycol, macrogol, pentaerythritol); stimulant laxatives (e.g. bisacodyl, senna (also referred to as senna glycosides or sennosides), hydroxyanthracene glycosides, phenolphthalein, oxyphenisatine, dantron, bisoxatin, sodium picosulfate); stool softener laxatives (also referred to as emollient agents; e.g. arachis oil, liquid paraffin, docusate sodium (dioctyl sodium sulfosuccinate)); saline laxative agents (e.g. sodium phosphate, sodium citrate, sodium tartrate; sodium sulphate, magnesium citrate, magnesium hydroxide, magnesium sulphate, magnesium carbonate, magnesium hydroxide, magnesium oxide, magnesium peroxide); lubricant laxatives (e.g. mineral oil, glycerol); serotonin agonist laxatives (e.g. cisapride, tegaserod, prucalopride); peripheral opioid antagonist laxatives alvimopan, methylnaltrexone, naloxegol; chloride channel activator laxatives (e.g. lubiprostone); castor oil; and linaclotide.

The further CF pharmaceutical may conveniently be applied in effective amounts before, simultaneously with or following the alginate oligomer and/or CFTR modulator. Conveniently the further CF pharmaceutical is applied at substantially the same time as the alginate oligomer and/or CFTR modulator or afterwards. In other embodiments the further CF pharmaceutical may conveniently be applied or administered before the alginate oligomer and/or CFTR modulator. The further CF pharmaceutical can also be given (e.g. administered or delivered) repeatedly at time points appropriate for the agent used. The skilled person is able to devise a suitable dosage regimen. In long term treatments the alginate oligomer and/or CFTR modulator can also be used repeatedly. The alginate oligomer and/or CFTR modulator can be applied as frequently as the further CF pharmaceutical, or more or less frequently. The frequency required may depend on the location of the mucosal surface to which the alginate oligomer is administered and also the overall nature of the clinical condition, (e.g. CF) displayed by the particular patient undergoing treatment.

The alginate oligomers and CFTR modulators proposed for use according to the invention and the further CF pharmaceutical (or further therapeutically active agent), may for example be administered together, in a single pharmaceutical formulation or composition, separately, or two together and the third separately (i.e. separate, sequential or simultaneous administration). Thus, effective amounts of the alginate oligomers and/or CFTR modulators of the invention and the further CF pharmaceutical may be combined, e.g. in a pharmaceutical kit or as a combined ("combination") product.

The invention therefore also provides products (e.g. a pharmaceutical kit or a combined ("combination") product) or compositions (e.g. a pharmaceutical composition) wherein the product or composition comprises an alginate oligomer and CFTR modulator as herein defined and a further CF pharmaceutical (or further therapeutically active agent), e.g. those described above. Combinations comprising an alginate oligomer and CFTR modulator as herein defined and an antibiotic, an antifungal, an NSAID, a bronchodilator, a corticosteroid, a laxative and/or a mucus viscosity reducing agent are preferred. Combinations comprising an alginate oligomer and a CFTR modulator as herein defined and an antibiotic, an antifungal, a laxative and/or a mucus viscosity reducing agent are especially preferred. Such pharmaceutical products and pharmaceutical compositions are preferably adapted for use in the medical methods of the invention.

The use of alginate oligomers and CFTR modulators as herein defined to manufacture such pharmaceutical products and pharmaceutical compositions for use in the medical methods of the invention is also contemplated.

The invention will be further described with reference to the following non-limiting Examples.

Example 1

A patient previously diagnosed with CF is identified and consent for therapeutic treatment is obtained. A film-coated tablet containing 150 mg ivacaftor, the inactive ingredients colloidal silicon dioxide, croscarmellose sodium, hypromellose acetate succinate, lactose monohydrate, magnesium stearate, microcrystalline cellulose, and sodium lauryl sulphate, and a film of carnauba wax, FD&C Blue #2, PEG 3350, polyvinyl alcohol, talc, and titanium dioxide is administered to the patient twice a day for at least 48 weeks. An inhalable powder containing 80% OligoG CF 5/20 (5-20mer alginate oligomer with at least 85% G residues) and 20% of other DPI excipients is also administered to the patient via a DPI inhaler twice daily resulting in a total daily dose of 2 g. The patient's clinical indicators of CF are observed, including their forced expiratory volume in 1 second ($FEV_1$) and sweat chloride levels.

Example 2

Patients previously diagnosed with CF are identified and consent for therapeutic treatment is obtained. A film-coated tablet containing 25 mg, 50 mg, 100 mg, 200 mg, 250 mg, 400 mg or 600 mg lumacaftor, the inactive ingredients colloidal silicon dioxide, croscarmellose sodium, hypromellose acetate succinate, lactose monohydrate, magnesium stearate, microcrystalline cellulose, and sodium lauryl sulphate, and a film of carnauba wax, FD&C Blue #2, PEG 3350, polyvinyl alcohol, talc, and titanium dioxide is administered to each patient twice a day for at least 28 days. An inhalable powder containing 80% OligoG CF 5/20 (5-20mer alginate oligomer with at least 85% G residues) and 20% of other DPI excipients is also administered to the patient via a DPI inhaler twice daily resulting in a total daily dose of 2 g. The patients' clinical indicators of CF are observed, including their forced expiratory volume in 1 second ($FEV_1$) and sweat chloride levels.

Example 3

Patients previously diagnosed with CF are identified and consent for therapeutic treatment is obtained. Powdered ataluren is administered in water or milk three times a day (at breakfast, lunch and dinner) over a period of at least 48 weeks. Amounts administered are as follows: (i) 4 mg/kg at breakfast, 4 mg/kg at lunch, 8 mg/kg at dinner; or (ii) 10 mg/kg at breakfast, 10 mg/kg at lunch, 20 mg/kg at dinner. Two enteric coated tablets containing 80% w/v of OligoG CF 5/20 oligomer and 20% of other excipients are also administered to the patient orally twice daily resulting in a total daily dose of 2 g. The patient's clinical indicators of CF are observed, including their sweat chloride levels and gut transit times.

Example 4

A patient previously diagnosed with CF is identified and consent for therapeutic treatment is obtained. The tablet of Example 1 is administered twice a day for at least 48 weeks. The enteric coated tablets of Example 3 are also administered as described in Example 3. The patient's clinical indicators of CF are observed, including their sweat chloride levels and gut transit times.

Example 5

Patients previously diagnosed with CF are identified and consent for therapeutic treatment is obtained. The tablets of Example 2 are administered to each patient twice a day for at least 28 days. The enteric coated tablets of Example 3 are also administered as described in Example 3. The patients' clinical indicators of CF are observed, including their sweat chloride levels and gut transit times.

Example 6

A patient previously diagnosed with CF is identified and consent for therapeutic treatment is obtained. The tablet of Example 1 is administered twice a day for at least 48 weeks. Enteric coated granules containing 80% w/v of OligoG CF 5/20 oligomer and 20% of other excipients are also administered to the patient orally twice daily resulting in a total daily dose of 2 g. The patient's clinical indicators of CF are observed, including their sweat chloride levels and gut transit times.

Example 7

A patient previously diagnosed with CF is identified and consent for therapeutic treatment is obtained. Two multi-layered tablets, both containing 75 mg ivacaftor and 0.5 g OligoG CF 5/20 oligomer, wherein the OligoG CF 5/20 oligomer is carried in an outer layer coating an interior carrying the CFTR modulator, are administered twice a day (i.e. a 2 g total daily dose of OligoG) for at least 48 weeks. The patient's clinical indicators of CF are observed, including their sweat chloride levels and gut transit times.

Example 8

A patient previously diagnosed with CF is identified and consent for therapeutic treatment is obtained. A 2 g total daily dose of OligoG and 300 mg total daily dose of ivacaftor is administered orally bis daily for at least 5 days in the form of multi-layered tablets consisting of four distinct layers, each layer containing either OligoG or ivacaftor, wherein the layered arrangement is adapted to prolong the release of OligoG and ivacaftor in the intestinal tract. The patient's clinical indicators of CF are observed, including their sweat chloride levels and gut transit times.

Example 9—OligoG Potentiation of the Partial Restoration of CFTR-Mediated Anion Secretion by VX-809 in Rectal Biopsies from F508del/F508del Human Patients Briefly, rectal biopsies were obtained from CF patients homozygous for the F508del mutation using the ECFS-CTN-approved standardised procedure and mounted in Ussing chambers (EM-LVSYS-4; P2407C slider; Physiologic Instruments, San Diego) in Meyler buffer (all in mM: Hepes 10; $Na_2HPO_4$ 0.3; $NaH_2PO_4$ 0.4; $MgCl_2$ 1.0; $CaCl_2$ 1.3; KCl 4.7; NaCl 128; $NaHCO_3$ 20.2; D-Glucose 10; pH 7.4; osmolarity 300 mOsm). Intestinal current measurements (ICM) were then performed as described below.

Subsequently, the medium in both chambers was replaced by biopsy-storage buffer including antibiotics (RPMI-1640 medium with L glutamine, sodium bicarbonate, sterile filtered, pH 7.4, indomethacin (10 μM), penicillin (40 μg/ml), streptomycin (90 μg/ml), ciprofloxacin (20 μg/ml) and metronidazole (200 μg/ml)), and biopsies were treated for 10 min at the luminal side in medium containing OligoG (1.5%; osmolarity 75 mOsm) or mannitol (75 mM) and at the serosal side in medium containing mannitol (75 mM). At 10 mins of OligoG/mannitol treatment VX-809 was added to both sides of each biopsy (final concentration of 5 μM). Following overnight (18 h) incubation with continued carbogen gassing (95% $O_2$/5% $CO_2$; medium flow rate), the medium was be replaced by regular perfusion buffer (Meyler buffer) and ICM was repeated. The enhancement (rescue) of F508del-CFTR-mediated chloride secretory currents in the mannitol/VX-809-treated biopsies was compared with the OligoG/VX-809-treated biopsies.

ICM was measured as short-circuit current ($I_{sc}$), a direct measure for the net movement of ions across the epithelium, in response to the following regime of ion channel modulators.

40 mins prior to exposure to the first ion channel modulator (amiloride) biopsies were bathed in Indomethacin-Meyler buffer (all in mM: Hepes 10; $Na_2HPO_4$ 0.3; $NaH_2PO_4$ 0.4; $MgCl_2$ 1.0; $CaCl_2$ 1.3; KCl 4.7; NaCl 128; $NaHCO_3$ 20.2; D-Glucose 10; Indomethacin 0.01; pH 7.4; osmolarity 300 mOsm) and replenished with preheated stock repetitively every 10 min (time points 10, 20, 30 min) to reach an optimal tissue precondition. Short-circuit current ($I_{sc}$) was then monitored. Once a baseline reading was established amiloride was added to the mucosal compartment to a final concentration of 100 µM. After a minimum of 5 min in amiloride (or until $I_{sc}$ was stable) forskolin and IBMX were added to a final concentration of 10 µM and 100 µM, respectively, to both the mucosal and serosal compartments. After a minimum of 10 min in forskolin/IBMX, genistein was added to a final concentration of 10 µM to the mucosal and serosal compartments. After a minimum of 5 min in genistein, carbachol was added to a final concentration of 100 µM to the serosal compartment. After a minimum of 10 min in carbachol (or until $I_{sc}$ was stable) histamine was added to a final concentration of 500 µM to the serosal compartment.

Treatment with 10 µM indomethacin (mucosal and serosal compartments) was to reduce CFTR dependent Cl$^-$ secretion to baseline. Treatment with amiloride (100 µM, mucosal compartment) was to block Na$^+$ absorption. Tissues were then stimulated with 10 µM forskolin+100 µM IBMX (mucosal and serosal compartments) to raise intracellular cAMP. Tissues were then stimulated with carbachol (100 µM, serosal) to activate basolateral K$^+$ channels and augment CFTR-dependent currents. These manoeuvres have been shown to isolate CFTR activity, producing a large CFTR-dependent Cl$^-$ secretory current (serosal to mucosal direction) that is evident in the presence of functional CFTR at the mucosal plasma membrane. In the absence of CFTR, these manoeuvres can produce a small secretory K$^+$ current with a downward deflection in the $I_{sc}$.

Figure 2:
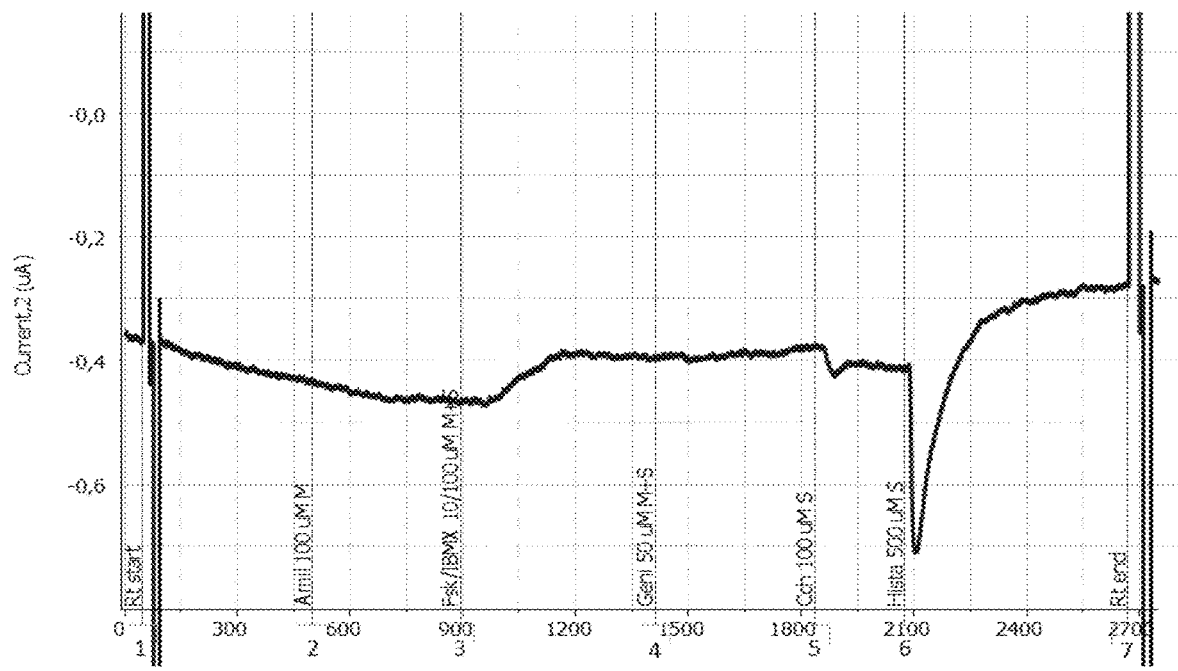
FIG. 2 shows $I_{se}$ traces measuring CFTR-mediated anion secretion in rectal biopsies from F508del/F508del human patients either as untreated control (A) or pretreated for 18 h with 5 µM VX-809 (M and S) together with 1.5% OligoG (M) at 37° C. (B).
Figure 2:
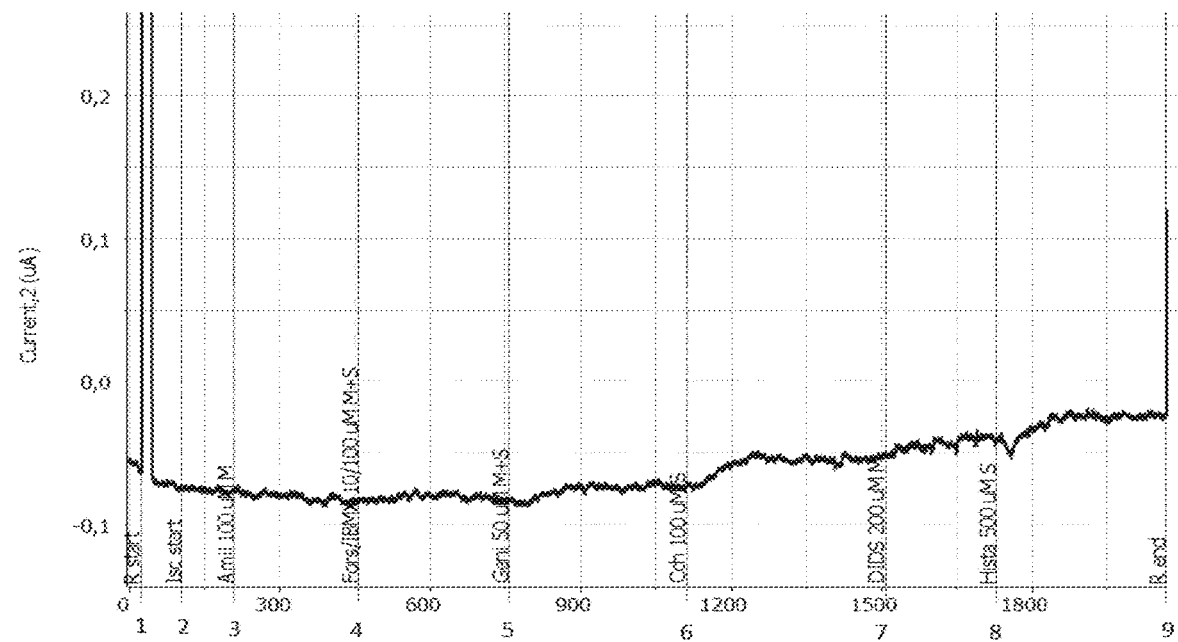

As can be seen from FIGS. 1A and 1B, treatment of biopsies with VX-809 alone partially restores CFTR-mediated anion secretion as measured by $I_{sc}$. As can been seen from FIGS. 1B and 2B, the presence of 1.5% OligoG beginning 10 mins prior to treatment with VX-809 potentiates this restoration of CFTR-mediated anion secretion. When $\Delta ISM_{forskolin-carbachol}$ was calculated for biopsies treated for 18 h with 5 µM VX-809 (M and S) alone or together with 1.5% OligoG (M), results of 9.1±1.8 µAmp/cm$^2$ (N=2; n=4) and 15.6±3.2 µAmp/cm$^2$ (N=2; n=4) were obtained. $\Delta ISM_{forskolin-carbachol}$ correlates negatively with CFTR dysfunction and thus these results show that 1.5% OligoG (M) potentiates the action of 5 µM VX-809 (M and S) over the course of an 18 hr treatment.

The invention claimed is:

1. A method for the treatment of a condition in a subject arising from or associated with CFTR dysfunction, said method comprising administering to said subject an effective amount of lumacaftor (3-[6-[[1-(2,2-difluoro-1,3-benzodioxol-5-yl)cyclopropanecarbonyl]amino]-3-methylpyridin-2-yl]benzoic acid) together with an effective amount of an alginate oligomer of 2 to 50 monomer residues, at least 70% of which are G residues.

2. The method of claim 1, wherein said condition is a respiratory disorder or a complication thereof.

3. The method of claim 2 wherein the respiratory disorder is an obstructive respiratory disorder, or wherein the respiratory disorder is characterized by a chronic inflammatory state, airway remodeling and exacerbations due to respiratory tract infections.

4. The method of claim 1, wherein said condition is cystic fibrosis (CF), non-compound CFTR gene mutation heterozygosity, abnormal mucus clearance in the respiratory tract and/or breathing difficulties resulting from chronic particulate inhalation, COPD, chronic bronchitis, emphysema, bronchiectasis, asthma or chronic sinusitis, or a complication thereof.

5. The method of claim 1, wherein said condition is CF or a complication thereof.

6. The method of claim 1, wherein said treatment comprises the treatment of a complication of said condition, wherein said complication is selected from the group consisting of:
  (i) a complication of the respiratory tract and/or cardiovascular system;
  (ii) a complication of a paranasal sinus;
  (iii) a complication of the GI tract;
  (iv) a complication of the pancreas;
  (v) a complication of the liver; and
  (vi) a fertility complication.

7. The method of claim 6 wherein said complication is or involves an infection of the respiratory tract or results from stagnant mucus in the GI tract.

8. The method of claim 1, wherein the alginate oligomer has a degree of polymerization (DP), or a number average degree of polymerization (DPn) of 4 to 50, 4 to 35, 4 to 30, 4 to 25, 4 to 22, 4 to 20, 4 to 18, 4 to 16 or 4 to 14.

9. The method of claim 1, wherein the alginate oligomer has a degree of polymerization (DP), or a number average degree of polymerization (DPn) of
  (i) 6 to 50, 6 to 35, 6 to 30, 6 to 25, 6 to 22, 6 to 20, 6 to 18, 6 to 16 or 6 to 14, or
  (ii) 8 to 50, 8 to 35, 8 to 30, 8 to 25, 10 to 25, 10 to 22, 10 to 20, 10 to 18, or 10 to 15.

10. The method of claim 1,
  wherein the alginate oligomer has at least 80%, or at least 85%, or at least 90%, or at least 95% G residues.

11. The method of claim 10, wherein at least 80% of the G residues are arranged in G-blocks.

12. The method of claim 1, wherein said alginate oligomer is administered to the subject in an amount sufficient to achieve a local concentration of the alginate oligomer of 1 to 10% w/v, 1.5 to 6% w/v or 2 to 6% w/v at at least part of a mucosal surface with CFTR dysfunction.

13. The method of claim 1, wherein said alginate oligomer and said lumacaftor are both administered enterally, parenterally, topically or by inhalation.

14. The method of claim 13 wherein said enteral administration is oral and/or rectal, and said parenteral administration is direct intrahepatic or intrapancreatic injection.

* * * * *

UNITED STATES PATENT AND TRADEMARK OFFICE
CERTIFICATE OF CORRECTION

PATENT NO. : 10,751,363 B2
APPLICATION NO. : 15/560984
DATED : August 25, 2020
INVENTOR(S) : Arne Dessen It is certified that error appears in the above-identified patent and that said Letters Patent is hereby corrected as shown below:

On the Title Page

Column 1, Item (54), Line 1, under Title, delete "ALIGINATE" and insert --ALGINATE--.

On Page 2, Column 1, Item (56), Line 9, under Other Publications, delete "ErtesvÅag" and insert --Ertesvag--.

On Page 2, Column 2, Item (56), Line 15, under Other Publications, delete "AF508" and insert --ΔF508--.

In the Specification

In Column 1, Line 1, delete "ALIGINATE" and insert --ALGINATE--.

In Column 9, Line 32, delete "$I_{se}$" and insert --$I_{SC}$--.

Signed and Sealed this
First Day of December, 2020

Andrei Iancu
*Director of the United States Patent and Trademark Office*